United States Patent
Ma et al.

(10) Patent No.: US 12,224,042 B2
(45) Date of Patent: Feb. 11, 2025

(54) DEVICES AND METHODS FOR GENOME SEQUENCING

(71) Applicant: Western Digital Technologies, Inc., San Jose, CA (US)

(72) Inventors: Wen Ma, Sunnyvale, CA (US); Tung Thanh Hoang, San Jose, CA (US); Daniel Bedau, San Jose, CA (US); Justin Kinney, San Jose, CA (US)

(73) Assignee: Sandisk Technologies, Inc., Milpitas, CA (US)

( * ) Notice: Subject to any disclaimer, the term of this patent is extended or adjusted under 35 U.S.C. 154(b) by 643 days.

(21) Appl. No.: 16/908,581

(22) Filed: Jun. 22, 2020

(65) Prior Publication Data

US 2021/0398618 A1    Dec. 23, 2021

(51) Int. Cl.
*G16B 40/20* (2019.01)
*C12Q 1/6869* (2018.01)
*G16B 30/10* (2019.01)

(52) U.S. Cl.
CPC ........... *G16B 40/20* (2019.02); *C12Q 1/6869* (2013.01); *G16B 30/10* (2019.02)

(58) Field of Classification Search
CPC ....... G16B 40/20; G16B 30/10; C12Q 1/6869
See application file for complete search history.

(56) References Cited

U.S. PATENT DOCUMENTS

| 8,634,247 B1 | 1/2014 | Sprouse et al. |
| 8,817,541 B2 | 8/2014 | Li et al. |

(Continued)

FOREIGN PATENT DOCUMENTS

| CA | 2854084 C | 11/2019 |
| CN | 101866357 A | 10/2010 |

(Continued)

OTHER PUBLICATIONS

Garro et al.; "Using a programmable network switch TCAM to find the best alignment of two DNA sequences"; Nov. 1, 2016; IEEE 36th Central American and Panama Convention (CONCAPAN XXXVI); available at: https://ieeexplore.ieee.org/document/7942372, 5 Pages.

(Continued)

*Primary Examiner* — Karlheinz R. Skowronek
*Assistant Examiner* — Emilie A Neulen
(74) *Attorney, Agent, or Firm* — Barry IP Law, P.C.

(57) ABSTRACT

A device includes arrays of Non-Volatile Memory (NVM) cells. Reference sequences representing portions of a genome are stored in respective groups of NVM cells. Exact matching phase substring sequences representing portions of at least one sample read are loaded into groups of NVM cells. One or more groups of NVM cells are identified where the stored reference sequence matches the loaded exact matching phase substring sequence using the arrays at Content Addressable Memories (CAMs). Approximate matching phase substring sequences are loaded into groups of NVM cells. One or more groups of NVM cells are identified where the stored reference sequence approximately matches the loaded approximate matching phase substring sequence using the arrays as Ternary CAMs (TCAMs). At least one of the reference sequence and the approximate matching phase substring sequence for each group of NVM cells includes at least one wildcard value when the arrays are used as TCAMs.

26 Claims, 10 Drawing Sheets

(56) References Cited

U.S. PATENT DOCUMENTS

| | | | |
|---|---|---|---|
| 9,098,403 | B2 | 8/2015 | Sprouse et al. |
| 9,443,590 | B2 | 9/2016 | Petti |
| 9,600,625 | B2 | 3/2017 | Asadi et al. |
| 9,639,501 | B1 | 5/2017 | Gazit et al. |
| 9,734,284 | B2 | 8/2017 | Olson |
| 2010/0138376 | A1 | 6/2010 | Avis et al. |
| 2013/0246698 | A1 | 9/2013 | Estan et al. |
| 2014/0136120 | A1 | 5/2014 | Colwell et al. |
| 2014/0172824 | A1 | 6/2014 | Musuvathi et al. |
| 2014/0347933 | A1* | 11/2014 | Lee .................. G11C 15/04 365/185.17 |
| 2014/0371110 | A1 | 12/2014 | Rooyen et al. |
| 2017/0235876 | A1 | 8/2017 | Jaffe et al. |
| 2017/0337325 | A1 | 11/2017 | Olson |
| 2019/0214111 | A1 | 7/2019 | Alberti et al. |
| 2021/0201163 | A1 | 7/2021 | Kalsi et al. |

FOREIGN PATENT DOCUMENTS

| | | |
|---|---|---|
| EP | 2759952 A1 | 7/2014 |
| EP | 3673386 A1 | 7/2020 |
| EP | 3673386 B1 | 7/2020 |

OTHER PUBLICATIONS

Khatamifard et al.; "Read Mapping Near Non-Volatile Memory"; arXiv:1709.02381; May 5, 2020; available at: https://arxiv.org/abs/1709.02381, 13 Pages.

Parag K Lala; "A CAM (Content Addressable Memory) Architecture for Codon Matching in DNA Sequences"; Current Journal of Applied Science and Technology; Jul. 10, 2015; available at https://www.journalcjast.com/index.php/CJAST/article/view/8357, 8 Pages.

International Search Report and Written Opinion dated Jun. 16, 2021 from International Application No. PCT/US2021/014952, 9 pages.

International Search Report and Written Opinion dated Oct. 22, 2020; International Application No. PCT/US2020/040568, 11 pages.

Canzar et al.; "Short Read Mapping: An Algorithmic Tour"; Mar. 2017; Proc IEEE Inst Electr Electron Eng.; 54 pages; available at: https://www.ncbi.nlm.nih.gov/pmc/articles/PMC5425171/pdf/nihms854488.pdf.

Jain et al.; "A fast adaptive algorithm for computing whole-genome homology maps"; Bioinformatics; 9 pages; Sep. 2018; available at: https://academic.oup.com/bioinformatics/article/34/17/1748/5093242.

Kim, et al.; "GRIM-Filter: Fast seed location filtering in DNA read mapping using processing-in-memory technologies"; BMC Genomics; vol. 19; Suppl. 2; May 9, 2018; 18 pages; available at: https://bmcgenomics.biomedcentral.com/articles/10.1186/s12864-018-4460-0.

Wilton et al.; "Faster sequence alignment through GPU-accelerated restriction of the seed-and-extend search space"; bioRxiv; Aug. 1, 2014; 7 pages; available at: https://www.biorxiv.org/content/10.1101/007641v1.full.

International Search Report and Written Opinion dated Oct. 27, 2020 from counterpart International Application No. PCT/US2020/040530, 10 pages.

Kaplan et al.; "A Resistive CAM Processing-in-Storage Architecture for DNA Sequence Alignment"; Aug. 21, 2017; IEEE Micro; vol. 37, No. 4; 9 pages; available at: https://ieeexplore.ieee.org/document/8013498.

Kaplan et al.; "BioSEAL: In-Memory Biological Sequence Alignment Accelerator for Large-Scale Genomic Data"; Jan. 17, 2019; 14 pages; available at: https://arxiv.org/ftp/arxiv/papers/1901/1901.05959.pdf.

Karam et al.; "Emerging Trends in Design and Applications of Memory-Based Computing and Content-Addressable Memories"; Jul. 15, 2015; Proceedings of the IEEE; vol. 103; 20 pages; available at: https://ieeexplore.ieee.org/document/7159147.

Khatamifard et al.; "A Non-volatile Near-Memory Read Mapping Accelerator"; Sep. 7, 2017; 12 pages; available at https://arxiv.org/abs/1709.02381.

Pending U.S. Appl. No. 16/820,711, filed Mar. 17, 2020, entitled "Devices and Methods for Locating a Sample Read in a Reference Genome", Justin Kinney.

Pending U.S. Appl. No. 16/821,849, filed Mar. 17, 2020, entitled "Reference-Guided Genome Sequencing", Justin Kinney.

Pending U.S. Appl. No. 16/822,010, filed Mar. 18, 2020, entitled "Reference-Guided Genome Sequencing", Justin Kinney.

Li et al.; "NVSim-CAM: A Circuit-Level Simulator for Emerging Nonvolatile Memory based Content-Addressable Memory"; Nov. 7, 2016; IEEE/ACM International Conference on Computer-Aided Design; 7 pages; available at: https://ieeexplore.ieee.org/document/7827579.

Chin et al.; "Nonhybrid, finished microbial genome assemblies from long-read SMRT sequencing data"; Nature.com; Nature Methods; May 5, 2013; p. 563-569; available at: https://www.nature.com/articles/nmeth.2474.

Houtgast et al.; "Hardware Acceleration of BWA-MEM Genomic Short Read Mapping for Longer Read Lengths"; Computational Biology and Chemistry; vol. 75; Aug. 2018; p. 54-64; available at https://doi.org/10.1016/j.compbiolchem.2018.03.024.

Liu et al.; "A Customized Many-Core Hardware Acceleration Platform for Short Read Mapping Problems Using Distributed Memory Interface with 3D-Stacked Architecture"; Journal of Signal Processing Systems; Dec. 3, 2016; p. 327-341; available at https://link.springer.com/article/10.1007/s11265-016-1204-8.

Xinyu Guo; "Design of A Systolic Array-Based FPGA Parallel Architecture for the BLAST Algorithm and Its Implementation"; The University of Toledo Digital Repository Theses and Dissertations; Aug. 2012 available at: http://citeseerx.ist.psu.edu/viewdoc/download?doi=10.1.1.917.6897&rep=rep1&type=pdf, 71 Pages.

Ye at al.; "DBG2OLC: Efficient Assembly of Large Genomes Using Long Erroneous Reads of the Third Generation Sequencing Technologies"; Nature.com; Scientific Reports; Aug. 30, 2016; 9 pages; available at: https://www.nature.com/articles/srep31900.

Lischer et al.; "Reference-guided de novo assembly approach improves genome reconstruction for related species"; BMC Bioinformatics; Nov. 10, 2017; 12 pages; available at https://bmcbioinformatics.biomedcentral.com/articles/10.1186/s12859-017-1911-6.

Hiatt et al.; "Parallel, tag-directed assembly of locally derived short sequence reads"; Nature.com; Nature Methods; Jan. 17, 2010; pp. 119-122; available at: https://www.nature.com/articles/nmeth.1416.

Gamaarachchi et al.; "Featherweight long read alignment using partitioned reference indexes"; Nature.com; Scientific Reports; Mar. 13, 2019; 12 pages; available at: https://www.nature.com/articles/s41598-019-40739-8.

Simpson et al.; "Efficient de novo assembly of large genomes using compressed data structures"; Genome Research; Dec. 7, 2011; 10 pages; available at: https://genome.cshlp.org/content/22/3/549.full?SID=896285ab-62e4-4258-9e15-5cef59a88f0c.

Huang et al.; "LW-FQZip 2: a parallelized reference-based compression of FASTQ files"; BMC Bioinformatics; Mar. 20, 2017; available at: https://bmcbioinformatics.biomedcentral.com/articles/10.1186/s12859-017-1588-x, 8 Pages.

Janin et al.; "BEETL-fastq: a searchable compressed archive for DNA reads"; Bioinformatics; vol. 30; Issue 19, Oct. 2014; pp. 2796-2801; available at: https://academic.oup.com/bioinformatics/article/30/19/2796/2422232.

Hwang et al.; "Privacy-Preserving Compressed Reference-Oriented Alignment Map Using Decentralized Storage"; IEEE Access; Aug. 17, 2018; 12 pages; available at: https://ieeexplore.ieee.org/document/8438866.

Oenning et al.; "CompStor Novos: low cost yet fast assembly-based variant calling for personal genomes"; bioRxiv; Cold Spring Harbor Laboratory; Dec. 4, 2018; 16 pages; available at: https://www.biorxiv.org/content/10.1101/486092v1.

Houtgast, et al.; "An FPGA-Based Systolic Array to Accelerate the BWA-MEM Genomic Mapping Algorithm"; Delft University of Technology; Jul. 1, 2015; available at: http://pure.tudelft.nl/ws/files/10410158/3210798/pdf, 8 Pages.

(56) References Cited

OTHER PUBLICATIONS

Huangfu, et al.; "RADAR: A 3D-ReRAM based DNA Alignment Accelerator Architecture"; Jun. 24, 2018; In Proceedings of the 55th Annual Design Automation Conference; https://seal.ece.ucsb.edu/sites/seal.ece.ucsb.edu/files/publications/a59-huangfu.pdf, 6 Pages.

McVicar, et al.; "FPGA Acceleration of Short Read Alignment"; arXiv preprint arXiv:1805.00106; Apr. 30, 2018; available at: http://arxiv.org/ftp/arxiv/papers/1805/1805.00106.pdf, 15 Pages.

Pfeiffer, et al.; "Hardware enhanced biosequence alignment"; International Conference on METMBS '05; vol. 5; Jun. 23, 2005; available at: http://citeseerx.ist.psu.edu/viewdoc/download?doi=10.1.1.85.5807&rep=rep1&type=pdf, 7 Pages.

International Search Report and Written Opinion dated Oct. 11, 2020 from counterpart International Application No. PCT/US2020/040570, 18 pages.

Altschul et al.; "Basic Local Alignment Search Tool"; May 15, 1990; Journal of molecular biology; available at: https://pubmed.ncbi.nlm.nih.gov/2231712/, 8 pages.

Guo et al; "A systolic array-based FPGA parallel architecture for the BLAST algorithm"; International Scholarly Research Notices; 2012; available at https://www.ncbi.nlm.nih.gov/pmc/articles/PMC4417556/, 11 pages.

Araujo et al.; "Multiple Sequence Alignment using Hybrid Parallel Computing"; 2017 IEEE 17th International Conference on Bioinformatics and Bioengineering, 6 pages.

Benkrid et al.; "A highly parameterized and efficient FPGA-based skeleton for pairwise biological sequence alignment"; IEEE Transactions on Very Large Scale Integration (VLSI) Systems 17.4 (2009): 561-570; Apr. 2009.

Shah et al; "Optimized and Portable FPGA-Based Systolic Cell Architecture for Smith-Waterman-Based DNA Sequence Alignment"; Journal of information and communication convergence engineering 14.1 (2016):26-34; Mar. 2016.

Lala et al.; "A CAM (Content Addressable Memory)-based architecture for molecular sequence matching"; Proceedings of the International Conference on Bioinformatics & Computational Biology (BIOCOMP), (Year: 2003).

Yu et al.; "A Smith-Waterman Systolic Cell"; Excerpt 13th International Conference, FPL 2003, Proceedings, p. 375-384 (Year: 2003).

Rauer et al.; "Accelerating Genomics Research with OpenCL and FPGAs"; Mar. 2016; Altera Corp.; 9 pgs.

Anonymous, "Content-addressable memory", Wikipedia, Retrieved from Internet URL: https://en.wikipedia.org/wiki/Content-addressable_memory, Retrieved on Dec. 18, 2023, 5 pages.

Li, H., et al.,: "A survey of sequence alignment algorithms for next-generation sequencing", Briefings in Bioinformatics, vol. II, Issue No. 5, pp. 473-483, (May 11, 2010).

\* cited by examiner

| Loaded Value | SL1SL2 | Stored Value | M1M2 | Result |
|---|---|---|---|---|
| 1 | 10 | 1 | 10 | Match |
| 0 | 01 | 1 | 10 | Mismatch |
| X | 11 | 1 | 10 | Match |
| 1 | 10 | 0 | 01 | Mismatch |
| 0 | 01 | 0 | 01 | Match |
| X | 11 | 0 | 01 | Match |
| 1 | 10 | X | 11 | Match |
| 0 | 01 | X | 11 | Match |
| X | 11 | X | 11 | Match |

FIG. 4A

| Loaded Value | SL1SL2 | Stored Value | M1M2 | Result |
|---|---|---|---|---|
| 1 | 10 | 1 | 10 | Match |
| 0 | 01 | 1 | 10 | Mismatch |
| ~~X~~ | ~~11~~ | ~~1~~ | ~~10~~ | ~~Match~~ |
| 1 | 10 | 0 | 01 | Mismatch |
| 0 | 01 | 0 | 01 | Match |
| ~~X~~ | ~~11~~ | ~~0~~ | ~~01~~ | ~~Match~~ |
| ~~1~~ | ~~10~~ | ~~X~~ | ~~11~~ | ~~Match~~ |
| ~~0~~ | ~~01~~ | ~~X~~ | ~~11~~ | ~~Match~~ |
| ~~X~~ | ~~11~~ | ~~X~~ | ~~11~~ | ~~Match~~ |

FIG. 4B

DEVICES AND METHODS FOR GENOME SEQUENCING

CROSS-REFERENCE TO RELATED APPLICATIONS

This application is related to co-pending application Ser. No. 16/821,849, filed on Mar. 17, 2020, and titled "REFERENCE-GUIDED GENOME SEQUENCING", the entire contents of which are hereby incorporated by reference. This application is also related to co-pending application Ser. No. 16/822,010, filed on Mar. 18, 2020, and titled "REFERENCE-GUIDED GENOME SEQUENCING", the entire contents of which are hereby incorporated by reference. This application is also related to co-pending application Ser. No. 16/820,711, filed on Mar. 17, 2020, and titled "DEVICES AND METHODS FOR LOCATING A SAMPLE READ IN A REFERENCE GENOME", the entire contents of which are hereby incorporated by reference.

BACKGROUND

Limitations in current DNA (deoxyribonucleic acid) and RNA (ribonucleic acid) sample handling lead to sample reads or portions of a sample genome having a generally unknown location in the sample genome. The sample reads must then be sequenced or put back into their locations in the sample genome. The two main types of genome sequencing are de novo sequencing and reference-aligned sequencing. Referenced-aligned sequencing uses a reference genome to locate the sample reads within the sample genome. De novo sequencing, on the other hand, does not typically use a reference genome, but instead compares sample reads to each other to locate the sample reads within the sample genome.

Both de novo and reference-aligned sequencing typically include phases of exact matching and approximate matching. Exact matching can be performed by, for example, seed and extend algorithms to find exact matches of a sample read within a reference genome to locate the sample read within the reference genome. However, due to sample read errors and mutations, it is generally not possible to exactly match or sequence all the sample reads in their locations in the sample genome. Approximate matching can use an algorithm, such as a Smith-Waterman algorithm or an Automata-based algorithm, to find a closest matching or best fit alignment in the sample genome.

Sequencing sample genomes generally requires a long processing time that can take hundreds to thousands of processor hours. Current devices for genome sequencing may include different arrangements of Static Random Access Memory (SRAM) Content Addressable Memory (CAM) or Ternary CAM (TCAM) for performing different phases of exact matching and approximate matching. However, such devices consume a large amount of power due to their volatile nature, and also consume a large area, such as by including six transistors per SRAM cell. The computing efficiency of genome sequencing systems still needs to improve by orders of magnitude. Accordingly, there is a need to improve devices used for genome sequencing in terms of processing efficiency, physical size, and energy consumption.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

FIG. 4A is an example truth table for the NVM cell of FIG. 3 when operating as a Ternary Content Addressable Memory (TCAM) according to one or more embodiments.

FIG. 4B is an example truth table for the NVM cell of FIG. 3 when operating as a Content Addressable Memory (CAM) according to one or more embodiments.

DETAILED DESCRIPTION

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

System Examples

Figure 1:
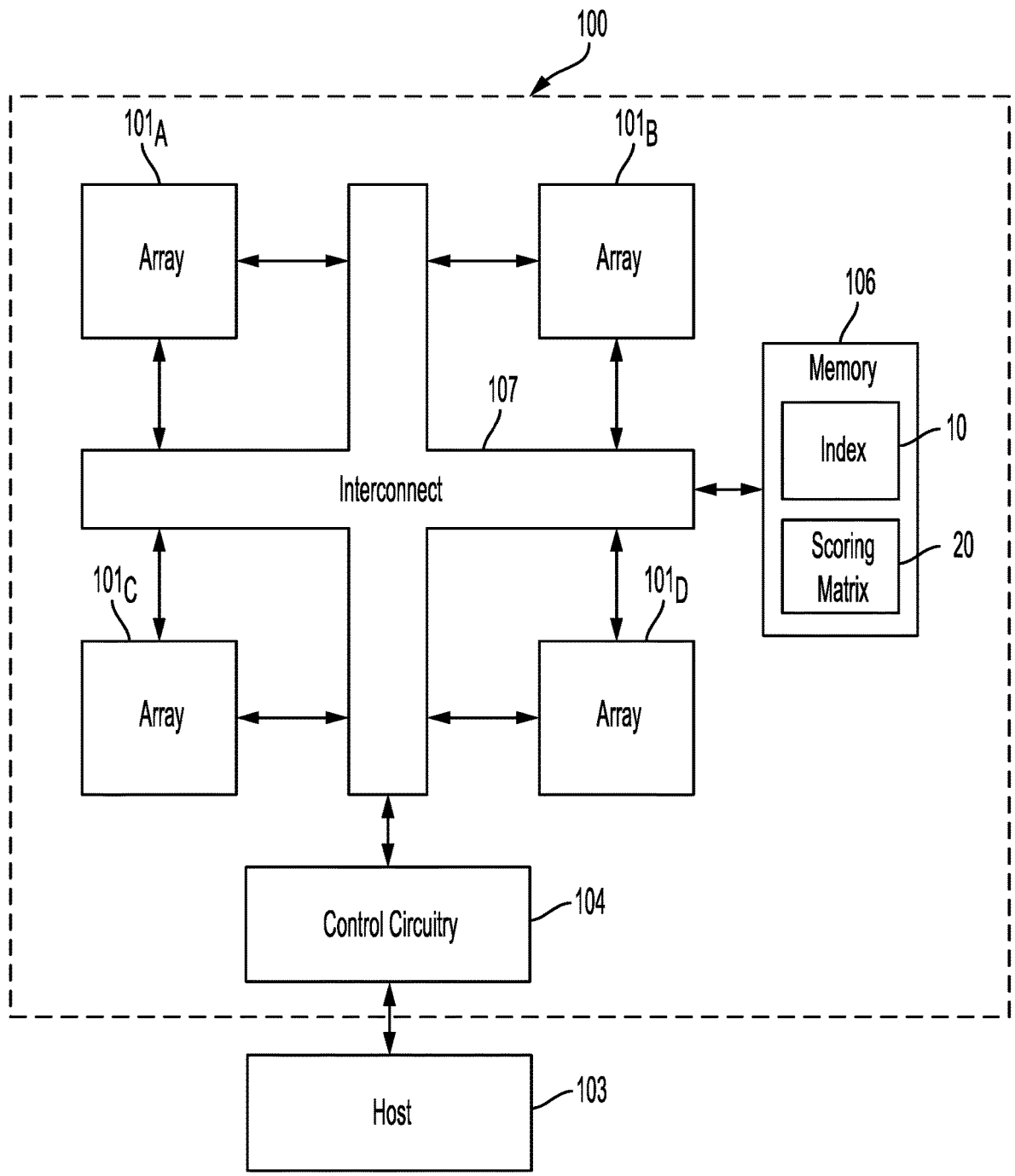
FIG. 1 is a block diagram of a device for genome sequencing including a plurality of arrays of Non-Volatile Memory (NVM) cells according to one or more embodiments.

FIG. 1 is a block diagram of device 100 for genome sequencing including a plurality of arrays of Non-Volatile Memory (NVM) cells according to one or more embodiments. Host 103 communicates with device 100 via control circuitry 104 to sequence sample reads for a sample genome. In some implementations, device 100 can provide host 103 with index 10 stored in memory 106 of device 100 indicating locations of the sample reads. In other implementations, device 100 may provide host 103 with another data structure or indication of locations of sample reads input to device 100.

The sample reads, or sample substring sequences taken from the sample reads, may initially be provided to device 100 by host 103 and/or by another device not shown in FIG. 1, such as by additional hosts, to determine locations of the sample reads for sequencing or aligning the sample reads in a sample genome from which the sample reads were taken.

In some implementations, a read device that generates the sample reads, such as an Illumina device (from Illumina, Inc. of San Diego, California) or a nanopore device may provide sample reads or sample substring sequences to device 100.

The substring sequences loaded into arrays 101 are compared to reference sequences stored in the arrays 101. The stored reference sequences represent portions of a genome. In cases where the sequencing is reference-aligned, reference sequences representing bases from a reference genome (e.g., human reference genome H38), or portions thereof, can be stored in the NVM cells of one or more arrays 101 for comparison to the loaded substring sequences. In cases where the sequencing is de novo, the sample reads can be compared to each other to identify areas of overlap to sequence or align the sample reads in the sample genome. In such cases, the NVM cells of one or more arrays 101 can store reference sequences representing portions of the sample genome for comparison to the loaded substring sequences.

For ease of description, the example embodiments in this disclosure will be described in the context of DNA sequencing. However, the embodiments of the present disclosure are not limited to DNA sequencing, and can be generally applied to any nucleic acid-based sequencing including RNA (ribonucleic acid) sequencing.

Host 103 can include, for example, a computer such as a desktop or server that may implement genome sequencing algorithms using device 100, such as a seed and extend algorithm for exact matching and/or a more computationally complex algorithm, such as a Burrows-Wheeler algorithm, an Automata-based algorithm, or Smith-Waterman algorithm for approximate matching of sample reads in a genome. Examples of Automata-based approximate matching algorithms can include, for example, Levenshtein Automata or String Independent Local Levenshtein Automata algorithms.

Host 103 and device 100 may or may not be physically co-located. For example, in some implementations, host 103 and device 100 may communicate via a network, such as by using a Local Area Network (LAN) or Wide Area Network (WAN), such as the internet, or a data bus or fabric. In addition, those of ordinary skill in the art will appreciate that other implementations may include multiple hosts 103 and/or multiple devices 100 for sequencing sample reads. In certain embodiments, host 103 and device 100 (or multiple hosts and devices) are integrated as a single device or system.

In the example of FIG. 1, each of arrays $101_A$, $101_B$, $101_C$, and $101_D$ of device 100 is configured to operate as a Content Addressable Memory (CAM) for exact matching, and to operate as a Ternary CAM (TCAM) for approximate matching depending on the encoding used for the reference sequences stored in the array and the substring sequences loaded into the array. As discussed in more detail below with reference to FIGS. 3, 4A, and 4B, arrays 101 include NVM cells that are structured to allow for the use of a wildcard value, which may also be referred to as a "don't care value" or "X value" when the array is used as a TCAM.

As compared to conventional Static RAM (SRAM) TCAM and SRAM CAM, the arrangements of NVM TCAM and CAM disclosed herein include non-volatile, solid-state memory that use less energy and consume less physical space. While the description herein refers to solid-state memory generally, it is understood that solid-state memory may comprise one or more of various types of memory devices such as flash integrated circuits, Chalcogenide RAM (C-RAM), Phase Change Memory (PC-RAM or PRAM), Programmable Metallization Cell RAM (PMC-RAM or PMCm), Ovonic Unified Memory (OUM), Resistive RAM (RRAM), NAND memory (e.g., Single-Level Cell (SLC) memory, Multi-Level Cell (MLC) memory (i.e., two or more levels), or any combination thereof), NOR memory, EEPROM, Ferroelectric Memory (FeRAM), Magnetoresistive RAM (MRAM), other discrete Non-Volatile Memory (NVM) chips, or any combination thereof. In some implementations, the cells in arrays 101 can include circuitry elements such as non-volatile registers, latches, or flip-flops.

As used herein, a cell generally refers to a memory location for storing a reference value or part of a reference value used to represent a nucleotide, referred to as a base in the present disclosure. In the example of FIG. 1, arrays 101 include cells that also include logic for comparing a loaded sample value to the stored reference value. The cells are arranged in groups in arrays 101 to store the reference sequences representing portions of a genome. In this regard, the reference values of the reference sequences are stored corresponding to the order of the cells in the group. Similarly, the sample values of the substring sequences are loaded into the cells of the group corresponding to the order of the cells of the group. The comparisons of the stored reference values to the loaded sample values for each group provide an indication of whether the stored reference sequence for the group matches (in the case of CAM operation) or approximately matches (in the case of TCAM operation) the loaded substring sequence. In some implementations, arrays 101 can include one or more systolic arrays where a reference value and/or a sample value may be passed to a next cell in another group of cells of an array 101.

Memory 106 of device 100 can include, for example, a volatile memory, such as DRAM or SRAM, for storing index 10 and scoring matrix 20. In other implementations, memory 106 can include an NVM, such as MRAM. As shown in FIG. 1, memory 106 stores index 10, which can be used by host 103 to indicate matching and/or approximately matching locations of a sample read within a genome, such as a reference genome or sample genome. In some implementations, index 10 can include a data structure, such as a bitmap or other data structure indicating an index or position in the genome corresponding to the groups of cells identified as storing matching and/or approximately matching sequences.

Control circuitry 104 may update index 10 for different sample substring sequences that are loaded into groups of cells of arrays 101. In some implementations, circuitry 104 may indicate a mean location in index 10 for a substring sequence that has multiple matching or approximately matching groups of cells. In other implementations, only a first matching or approximately matching group of cells for a particular substring sequence may be used, or control circuitry 104 may not update index 10 at all for a substring sequence that has more than a single group of cells storing matching sequences.

In addition, some implementations may not use an index or other data structure for indicating the location of groups of cells with matching or approximately matching sequences. For example, control circuitry 104 in some implementations may output indications of matching or approximately matching sequence locations directly to host 103.

Scoring matrix 20 can be used as part of an approximate matching algorithm, such as a Smith-Waterman algorithm. For example, scoring matrix 20 can be updated by control circuitry 104 to score matches and mismatches between reference sequences stored in arrays 101 and substring sequences loaded into arrays 101 to determine an optimal alignment for the substring sequence. As will be appreciated by those of ordinary skill in the art with reference to the present disclosure, scoring matrix 20 can include various forms of weighted data structures indicating, for example, relative expectations for insertions, deletions, and mutations.

Control circuitry 104 can include, for example, hardwired logic, analog circuitry and/or a combination thereof. In other implementations, control circuitry 104 can include one or more ASICs, microcontrollers, Digital Signal Processors (DSPs), FPGAs, and/or a combination thereof. In some implementations, control circuitry 104 can include one or more Systems on a Chip (SoCs), which may be combined with memory 106. In this regard, one or more arrays 101 and interconnect 107 may be integrated with control circuitry 104 and memory 106 as a single component or chip in some implementations.

In the example of FIG. 1, control circuitry 104 uses interconnect 107 for communication with arrays 101 and memory 106. In some implementations, arrays 101 and memory 106 may communicate directly via interconnect 107 without involvement of control circuitry 104. Interconnect 107 can include, for example, a bus for communication between arrays 101, control circuitry 104, and memory 106.

Figure 2:
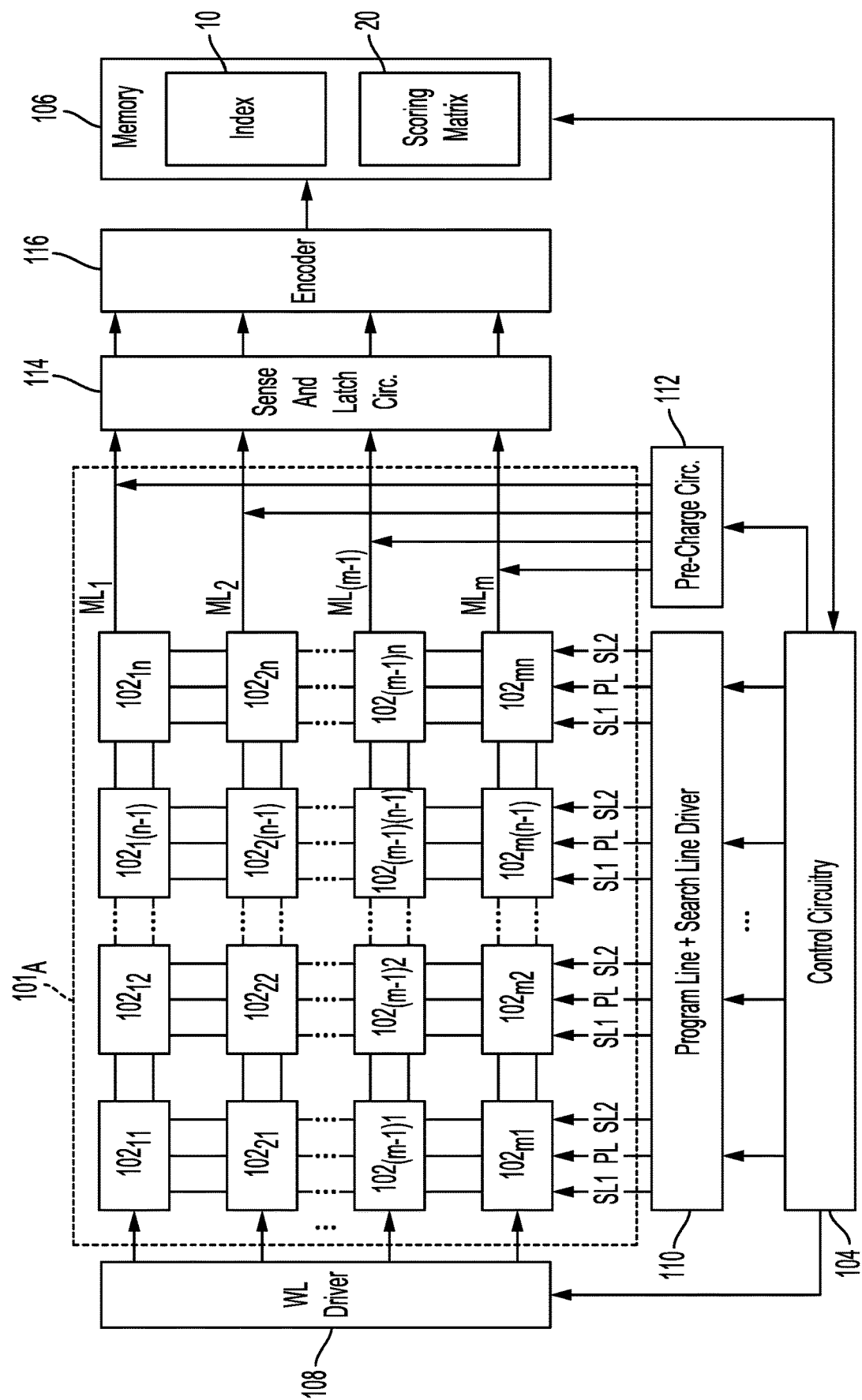
FIG. 2 is a block diagram of an array of NVM cells in the device of FIG. 1 according to one or more embodiments.

As noted above, circuitry of device 100, which may include control circuitry 104 and/or other circuitry (e.g., sense and latch circuitry $114_A$ and encoder $116_A$ in FIG. 2) is configured to identify groups of cells among the plurality of groups of cells in arrays 101 where the stored reference sequence matches or approximately matches the loaded substring sequence. As discussed in more detail below with reference to FIGS. 2 and 3, the identification of groups of cells with matching or approximately matching sequences may be made in some implementations by a state or charge of a match line shared by the cells in the group of cells.

As will be appreciated by those of ordinary skill in the art with reference to the present disclosure, other implementations may include a different number or arrangement of components than shown in the example of FIG. 1. For example, other implementations may combine host 103 and device 100 or may include a different number of arrays 101, memories 106, devices 100 and/or hosts 103. In this regard, device 100 may include many more arrays 101 than shown in FIG. 1 to allow for more concurrent or parallel comparisons to improve processing efficiency.

FIG. 2 is an example block diagram depicting NVM cells 102 in array $101_A$ of device 100 according to one or more embodiments. As shown in FIG. 2, array $101_A$ includes NVM cells 102 arranged in rows and columns in a cross-point array structure. As discussed in more detail below with reference to FIGS. 3 to 4B, array $101_A$ can operate as either a TCAM or a CAM depending on its programming. Each NVM cell 102 or pair of NVM cells is configured to store a reference value for comparison to a sample value loaded into the cell or pair of cells. Each base for a reference sequence and each base for a substring sequence can be represented by two bits, since there are four possible bases—Adenine (A), Guanine (G), Cytosine (C), and Thymine (T), in the case of DNA sequencing, for example. In some implementations, two adjacent cells 102 in the same row can store a reference value representing a reference base that is compared to a sample value representing a sample base loaded into the two adjacent cells. In other implementations, each cell can store a reference value representing a reference base that is compared to a sample value representing a sample base loaded into the cell. As discussed in more detail below with reference to FIGS. 3 to 4B, array $101_A$ when operating as a TCAM can use two cells to represent a reference value, but may either use one or two cells to represent a sample value when operating as a CAM depending on the use of wildcard values for reference values and/or sample values.

Control circuitry 104 controls Word Line (WL) driver $108_A$, and also controls program line and search line driver $110_A$ to program cells 102 in a particular row to store reference values for a reference sequence. In such an implementation, each row of cells 102 (e.g., cells $102_{11}$ to $102_{1n}$) can form a group of cells storing a reference sequence, and the reference sequences are stored corresponding to the order of the cells 102 in the group of cells. In the example of FIG. 2, array $101_A$ includes m groups of cells 102 that can each store a different reference sequence.

Control circuitry 104 also controls program line and search line driver 110 to load substring sequences into each group of cells 102 for comparison to the stored reference sequences, with the substring sequences corresponding to the order of the group of cells 102. In the example of FIG. 2, array $101_A$ includes n columns of cells, which allows for the loading of a substring sequence of length n if being used as a CAM or a length of n/2 if being used as a TCAM or a CAM in some implementations. The number of cells 102 in each group or row of cells, and therefore the length of the stored reference sequences and loaded substring sequences, can depend on a desired accuracy for locating the substring sequence in the reference genome.

In some implementations, the number of cells 102 in each group may be 40 cells, allowing for substring sequences representing 20 bases to be compared to reference sequences representing 20 bases in a TCAM mode. As discussed in more detail in co-pending application Ser. No. 16/820,711, filed on Mar. 20, 2020, and incorporated by reference above, substring sequences with lengths between 17 and 25 bases can provide a sufficient number of unique matches for most substring sequences with respect to reference genome H38. A substring length shorter than 17 bases will require a greater number of substring sequences from a sample read to determine a location of the sample read within reference genome H38, and a substring length shorter than 15 bases may fail to identify any unique matches within reference genome H38 for nearly all substring sequences attempted.

On the other hand, a substring length greater than 25 bases, would incur additional storage cost in terms of cells needed in arrays 101, and a greater computational cost due to the associated increase in operations needed, with little improvement in the number of unique matches. However, those of ordinary skill in the art will appreciate with reference to the present disclosure that a different substring length or a different number of cells in each group of cells may be preferred for other examples, such as when using a different reference genome or a portion of reference genome, as may be the case for medical diagnosis of a genetic condition related to a particular portion of a reference genome. In addition, different tradeoffs between computational cost, the number of cells, and accuracy in terms of a greater number of unique matches may also affect the number of cells used for each group of cells in arrays 101. For example, some implementations may provide for groups of cells 102 with 200 cells to correspond to a short sample read length of 200 bases. However, as discussed in more detail below with reference to FIG. 5, sample reads may be logically divided into multiple adjacent substring sequences for parallel or concurrent processing by multiple arrays 101.

Advantageously, each row of cells may be simultaneously or nearly simultaneously loaded with the same substring sequence in a single load operation or clock cycle to quickly identify any groups of cells 102 where the loaded substring sequence matches or approximately matches the reference sequences stored in the different groups of cells 102. In some implementations, each cell 102 can store two bits representing a reference value or half of a reference value if array $101_A$ is used as a TCAM, and each column may be loaded with two bits with high or low values (i.e., a "1" or "0" value) driven for the search lines, SL1 and SL2, for each column of cells 102 (e.g., cells $102_{11}$ to $102_{m1}$).

In other implementations, each cell 102 may store 3 bits instead of 2 bits, where the third bit is used as a mask bit or "don't care bit" for the wildcard value used for approximate matching. In such implementations, each cell 102 can store a reference value representing a reference base. When the mask bit is set, the match line will indicate a match regardless of the loaded sample value. In such implementations, a third search line (e.g., SL3) may be used to load a wildcard value as part of the substring sequence, which may result in a match regardless of the stored reference value.

The use of the groups or rows of cells 102 shown in FIG. 2 allow for substring sequences to be quickly compared against a large number of reference sequences in a single operation or clock cycle to improve processing efficiency. Array $101_A$ can include, for example, hundreds or thousands of rows or groups of cells to allow for a substring sequence to be compared to hundreds or thousands of reference sequences in a single operation or clock cycle. In some implementations, each group of cells 102 stores an overlapped reference sequence that has been shifted by one or another predetermined number of reference bases from the reference sequence stored in an adjacent group of cells.

Before loading the substring sequences, control circuitry 104 controls pre-charge circuitry 112 to charge a match line (ML) for each group or row of cells 102. In some implementations, pre-charge circuitry 112 can charge each match line to a high value (i.e., a "1" value). The pre-charge circuitry 112 may include, for example, a PMOS transistor. When the substring sequences are loaded into the groups of cells by programming search lines for each column, a single mismatch between the value stored in the cell and the value loaded into the cell in a group of cells will drive the match line for that group of cells to a low value (i.e., a "0" value). As discussed in more detail below, the use of a wildcard value will provide a match for the cell regardless of the value being compared to the wildcard value.

Sense and latch circuitry $114_A$ reads the value of each match line after the substring sequence has been loaded, and provides the sensed or read match line values to encoder $116_A$ to identify the match lines or groups of cells where the loaded substring sequence matches the stored reference sequence. Encoder $116_A$ can provide an address or other indication of the location of the group or groups of cells where the stored reference sequence matches the loaded substring sequence. In the example of FIG. 2, indications of the identified groups of cells, if any, can be added to index 10, which may include, for example, a bitmap or other data structure for indicating a location of the matching groups of cells, which in turn, can indicate an exact match or an approximate match between the stored reference sequence and the loaded substring sequence.

Those of ordinary skill in the art will appreciate that other implementations may include a different arrangement of circuitry or operation than shown and described for the example of FIG. 2. For example, other implementations may instead set match lines to a low value and indicate a low value for groups of cells that store a reference sequence that matches or approximately matches the loaded substring sequence. As another example variation, other implementations may not include memory 106, but may instead provide indications of matching or non-matching groups of cells directly to control circuitry 104.

Figure 3:
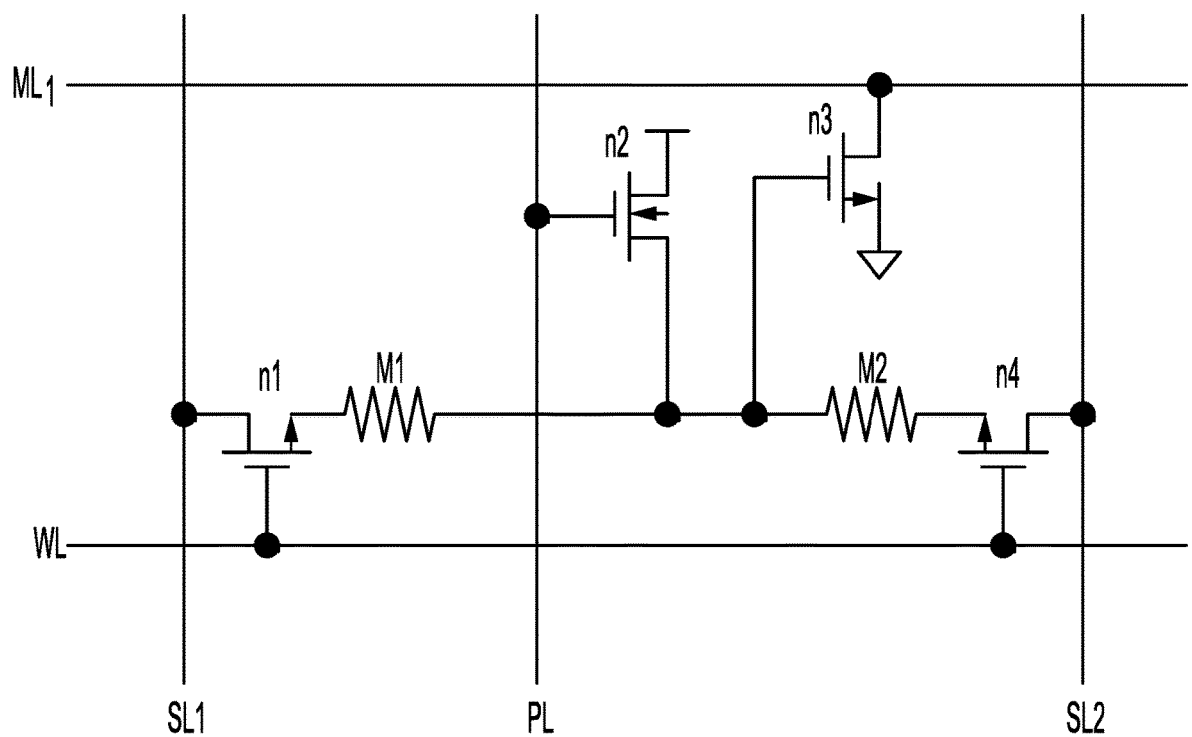
FIG. 3 is an example circuit diagram for an NVM cell in the device of FIG. 1 according to one or more embodiments.

FIG. 3 is an example circuit diagram for NVM cell $102_{12}$ of array $101_A$ from FIG. 2 according to one or more embodiments. The arrangement of FIG. 3 includes four transistors and two resistors. In some implementations, NVM cell $102_{12}$ can be a four transistor, two resistor RRAM, which can be referred to as a 4T2R-RRAM structure. Those of ordinary skill in the art will appreciate with reference to the present disclosure that other cell structures are possible, such as a two transistor, two resistor PCM, referred to as a 2T2-PCM structure, or a six transistor, two resistor MRAM structure, referred to as a 6T2-MTJ structure. As noted above, the use of a non-volatile cell structure, as opposed to a conventional volatile cell structure such as SRAM, allows for the array to consume less power by not having to refresh stored reference values. In addition, the use of less transistors than conventional SRAM TCAM cells, which may use sixteen transistors, allows for a higher density of storage, such as more Megabytes per square millimeter of the array. This can reduce the physical size of device 100 or allow for more arrays 101 in device 100 to reduce processing time.

In the example of FIG. 3, resistors M1 and M2 can be programmed to high or low resistance values by driving word line $WL_1$ and program line PL to store reference values. The search lines SL1 and SL2 can be driven to high or low values to correspond to input sample values, which can change the charge of the match line $ML_1$ depending on whether the charges of SL1 and M1 match and whether the charges of SL2 and M2 match. If the respective pairs of charges match, match line $ML_1$ retains its pre-charged state to indicate that the stored value matches the loaded value. If either of the respective pairs of charges do not match, match line $ML_1$ is pulled down and loses its pre-charged state to indicate that the stored value does not match the loaded value.

The example of cell $102_{12}$ in FIG. 3 stores two bits for comparison to two bits loaded into the cell via SL1 and SL2. Other implementations may use a different cell structure. For example, other cell structures may allow for a mask bit or third bit (e.g., a "trit") to be stored in the cell, and may further allow for a mask bit to be loaded into the cell. In such examples, the mask bit can serve as a wildcard value in the stored reference sequence or in the loaded substring sequence when array 101 is used as a TCAM. The state of match line $ML_1$ may then be maintained when the mask bit is set, regardless of the other bits stored or loaded into the cell. In the example structure of FIG. 3, a wildcard value stored in cell $101_{12}$ or loaded into cell $101_{12}$ can be obtained by the encoding of the reference values and the sample values, which is discussed in more detail below with reference to FIGS. 4A and 4B.

As shown in FIG. 4A, an input for a sample value from a substring sequence can have three different values of 1, 0, or a wildcard value of X depending on the programming of search lines SL1 and SL2. For example, when search lines SL1 and SL2 both have a value of 1, the loaded or input value is the wildcard value X. Similarly, when both resistors M1 and M2 have a value of 1, the stored value is the wildcard value X. The wildcard value for either of the loaded value or the stored value will result in a match, which will maintain the pre-charged state of the match line in the example cell structure of FIG. 3.

As noted above, each of the four bases—Adenine (A), Guanine (G), Cytosine (C), and Thymine (T), in the case of DNA sequencing, for example, can be represented by two bits. For example, A may be represented by 00, G represented by 01, C represented by 10, and T represented by 11. When operating as a TCAM and using the encoding of FIG. 4A, each cell 102 can store a value of 1, 0, or X, such that two adjacent cells 102 in a group or row of cells represent a stored reference base, such as A, G, C, or T.

In the example truth table of FIG. 4A, the programming of resistors M1 and M2 can provide a stored value of 1 when M1 is programmed to a high value (i.e., a value of 1 for M1) and M2 is programmed to a low value (i.e., a value of 0 for M2). On the other hand, a stored reference value of 0 is provided when M1 is programmed to a low value and M2 is programmed to a high value. When M1 and M2 are both programmed to high values (i.e., 11), the stored reference value is the wildcard value of X, meaning that the loaded or input value and the stored value will match regardless of the loaded value (i.e., the values programmed for S1 and S2).

The loaded values controlled by S1 and S2 follow a similar pattern where a high value of S1 and a low value for S2 results in an input value of 1, while a low value of S1 and a high value of S2 results in an input value of 0. As with the stored values controlled by M1 and M2, a high value for both S1 and S2 results in a loaded wildcard value of X, meaning that the loaded value and the stored value will match, regardless of the stored value (i.e., the values programmed for M1 and M2).

FIG. 4B is an example truth table for NVM cells 102 when operating as a CAM according to one or more embodiments. As shown in FIG. 4B, the programming of the cell is the same as for the operation as a TCAM in FIG. 4A, except that the encoding scheme has been varied to remove wildcard values of X from the programming, since they are not used for exact matching. In other words, S1 and S2 are no longer programmed as both high values (i.e., 11) and M1 and M2 are no longer programmed as both high values, so that wildcard values are no longer used. In such an implementation, a pair of cells 102 may still be used to represent a base, as with the example of FIG. 4A for operation as a TCAM. This can facilitate the reuse of the stored values in the cells for reference sequences so that the reference sequences do not need to be stored again when switching between exact matching and approximate matching phases of the sequencing for the same genome or portions thereof.

However, other implementations may allow for approximately twice as long reference and substring sequences when an array 101 operates as a CAM than when the array operates as a TCAM. In such implementations, each cell 102 can represent a single base with the loaded values and stored values for each cell being two bit values to represent four different bases. For example, instead of the stored values of two adjacent cells 102 representing a base, such as A with an input value of 00, the search lines S1 and S2 can each be programmed as 0 to represent loading a base value of 00 for A into a single cell 102. Similarly, M1 and M2 can each be programmed to represent a stored base for the cell 102.

Control circuitry 104 can be configured to vary the encoding scheme used for the reference sequences and substring sequences to switch between operation of an array as a CAM and as a TCAM. Such changes in the encoding scheme can include, for example, designating a value (e.g., a value of 11) as a wildcard value, and using this value for operation of the array in a TCAM mode, while refraining from using this value for operation of the array in a CAM mode. In other implementations, control circuitry 104 may vary the encoding scheme by using a third bit or state for a wildcard value. By varying the encoding scheme, it is ordinarily possible to selectively use arrays 101 as both CAMs and TCAMs, which can be used for exact matching phases and approximate matching phases of genome sequencing. This versatility of device 100 can improve the processing efficiency and reduce the size of device 100 for a given performance latency, as compared to conventional sequencing devices that use dedicated hardware for exact matching and approximate matching phases.

Those of ordinary skill in the art will appreciate with reference to the present disclosure that other encoding schemes or programming are possible than those shown in FIGS. 4A and 4B. For example, an input of 1 may instead result from a low value for SL1 and a high value for SL2, or the wildcard value X may instead result from two low values, as opposed to two high values, as in the example truth tables of FIGS. 4A and 4B.

Figure 5:
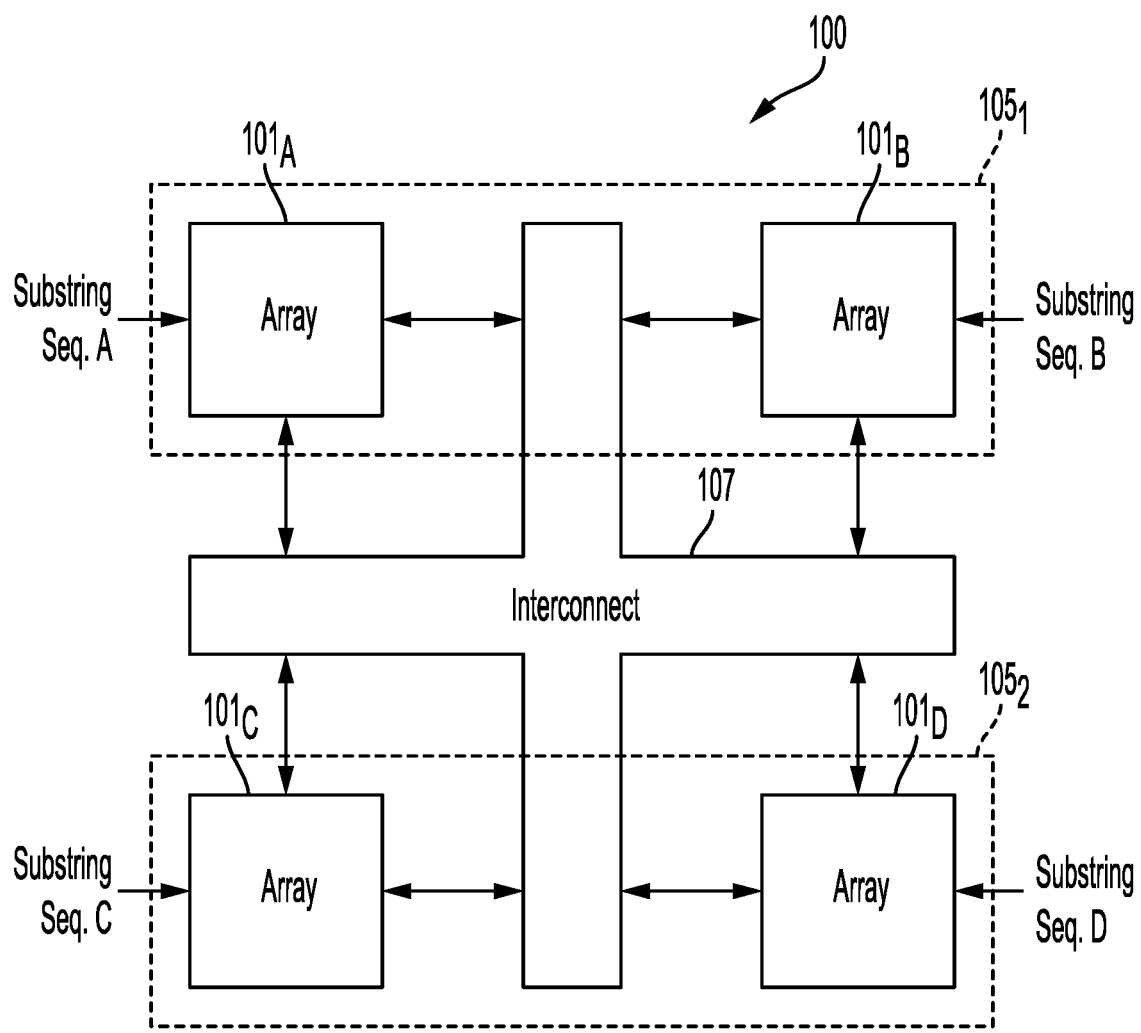
FIG. 5 is an example of the device of FIG. 1 being used to concurrently process substring sequences according to one or more embodiments.

FIG. 5 is an example of device 100 being used to concurrently process substring sequences according to one or more embodiments. As shown in FIG. 5, each of arrays $101_A$, $101_B$, $101_C$, and $101_D$ is concurrently loaded with a different substring sequence. In some implementations, this may be performed as a single load operation during a single clock cycle of control circuitry 104. Circuitry of device 100, such as sense and latch circuitry $114_A$ and encoder $116_A$ in FIG. 2, may then concurrently identify groups of cells where the stored reference sequence matches the substring sequence loaded into the array. Such circuitry may then provide an indication of the location of such matching sequences for updating an index stored in memory 106, such as index 10.

In the example of FIG. 5, substring sequence A and substring sequence B are two portions of the same sample read that are processed in parallel or concurrently to identify matching groups of cells where the loaded substring sequences match or approximately match the stored reference sequences. The number of different substring sequences taken from a sample read for comparison to reference sequences can depend on, for example, the length of the substring sequences, the length of the reference genome, the length of the sample read (e.g., a short read from an Illumina device of 250 or 300 bases versus a long read from a nanopore device of 5,000 bases), an accuracy of the process used to create the sample read, a reference genome being used for the stored reference sequences (e.g., reference genome H38), and a desired accuracy for locating the sample read within the reference genome or sample genome. In one example, short reads of 250 or 300 bases can be located in a reference genome with only a few matching substring sequences. Such an example may only use ten substring sequences from sample reads to generate enough matches to locate the sample reads in the reference genome.

Similarly, substring sequences C and D are two portions of a different sample read that are concurrently loaded with respect to each other and with respect to substring sequences A and B. Arrays $101_A$ and $101_B$ may be combined into a first array group $105_1$ for finding matches for the first sample read, and arrays $101_C$ and $101_C$ may be combined into a second array group $105_2$ for finding matches for the second sample read. As will be appreciated by those of ordinary skill in the art with reference to the present disclosure, the number of arrays 101 and/or groups of arrays may be much greater than those shown in FIG. 5, which is provided for the purposes of illustration. For example, a device of the present disclosure may include hundreds of arrays 101 to allow for the parallel or concurrent comparison of many portions of a sample read to reference sequences, the parallel or concurrent comparison of portions of many different sample reads to reference sequences, or the parallel or concurrent comparison of a single substring sequence to a large number of reference sequences. Such parallel or concurrent operation of arrays 101 can improve the processing efficiency of device 100.

Figure 6:
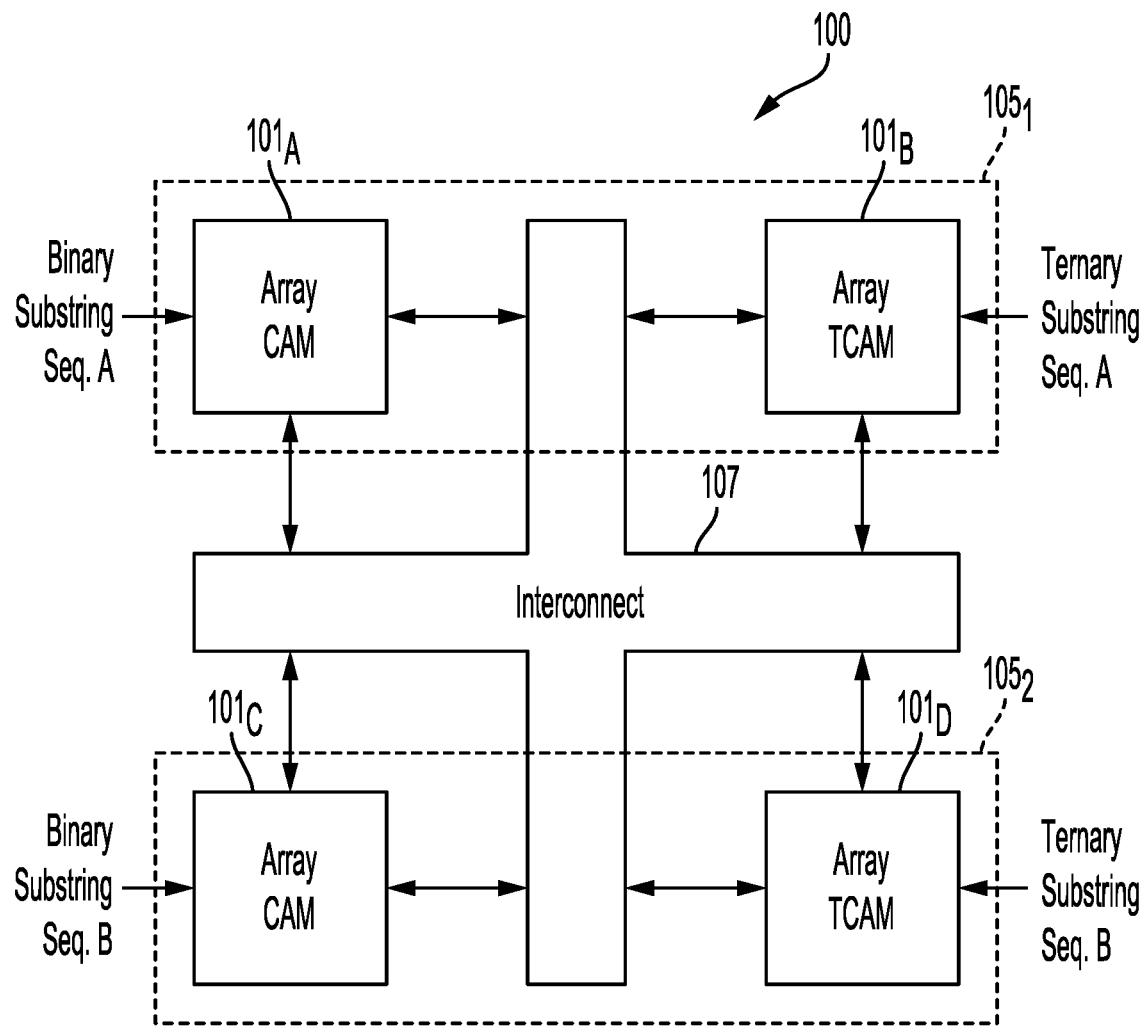
FIG. 6 is an example of the device of FIG. 1 being used to process exact matching phase and approximate matching phase substring sequences according to one or more embodiments.

FIG. 6 is an example of device 100 being used to concurrently process exact matching phase and approximate matching phase substring sequences according to one or more embodiments. Each of arrays $101_A$, $101_B$, $101_C$, and $101_D$ can operate as a CAM and as a TCAM depending on the encoding scheme used for the sequences stored and/or loaded in the array. As discussed above, the programming of wildcard values or X values allow for the operation of arrays 101 as TCAMs. These wildcard values can remain unused to allow for the operation of arrays 101 as CAMs. In some implementations, arrays 101 may switch from storing a reference value in two cells in a TCAM mode to storing a reference value in one cell due to the ability of each cell to store two bits that can represent any one of four bases in the CAM mode.

In the example of FIG. 6, the first group $105_1$ of arrays $101_A$ and $101_B$ concurrently performs an exact matching operation for substring sequence A using array $101_A$, and an approximate matching operation for substring sequence A using array $101_B$. Some of the input or loaded values in substring sequence A may be replaced with wildcard values and/or some of the stored reference sequence values may be replaced with wildcard values for operation of array $101_B$ as a TCAM.

Similarly, the second group $105_2$ of arrays $101_C$ and $101_D$ concurrently performs an exact matching operation for substring sequence B using array $101_C$, and an approximate matching operation for substring sequence B using array $101_D$. Some of the input values in substring sequence B may be replaced with wildcard values and/or some of the stored reference sequence values may be replaced with wildcard values for the operation of array $101_D$ as a TCAM. The operations of first group $105_1$ and second group $105_2$ may also be performed in parallel or concurrently with respect to each other. In other implementations, the use of arrays 101 within an array group 105 can occur in stages, as opposed to simultaneous operation. In such implementations, the performance of an approximate matching phase of sequencing may be dependent upon the completion of an exact matching phase, or vice-versa.

The ability of device 100 to use arrays 101 in either a TCAM mode or a CAM mode can allow for different searching granularity and for the use of the same hardware for both exact matching and approximating phases of genome sequencing. This can ordinarily reduce a footprint of hardware needed to genome sequencing.

Figure 7:
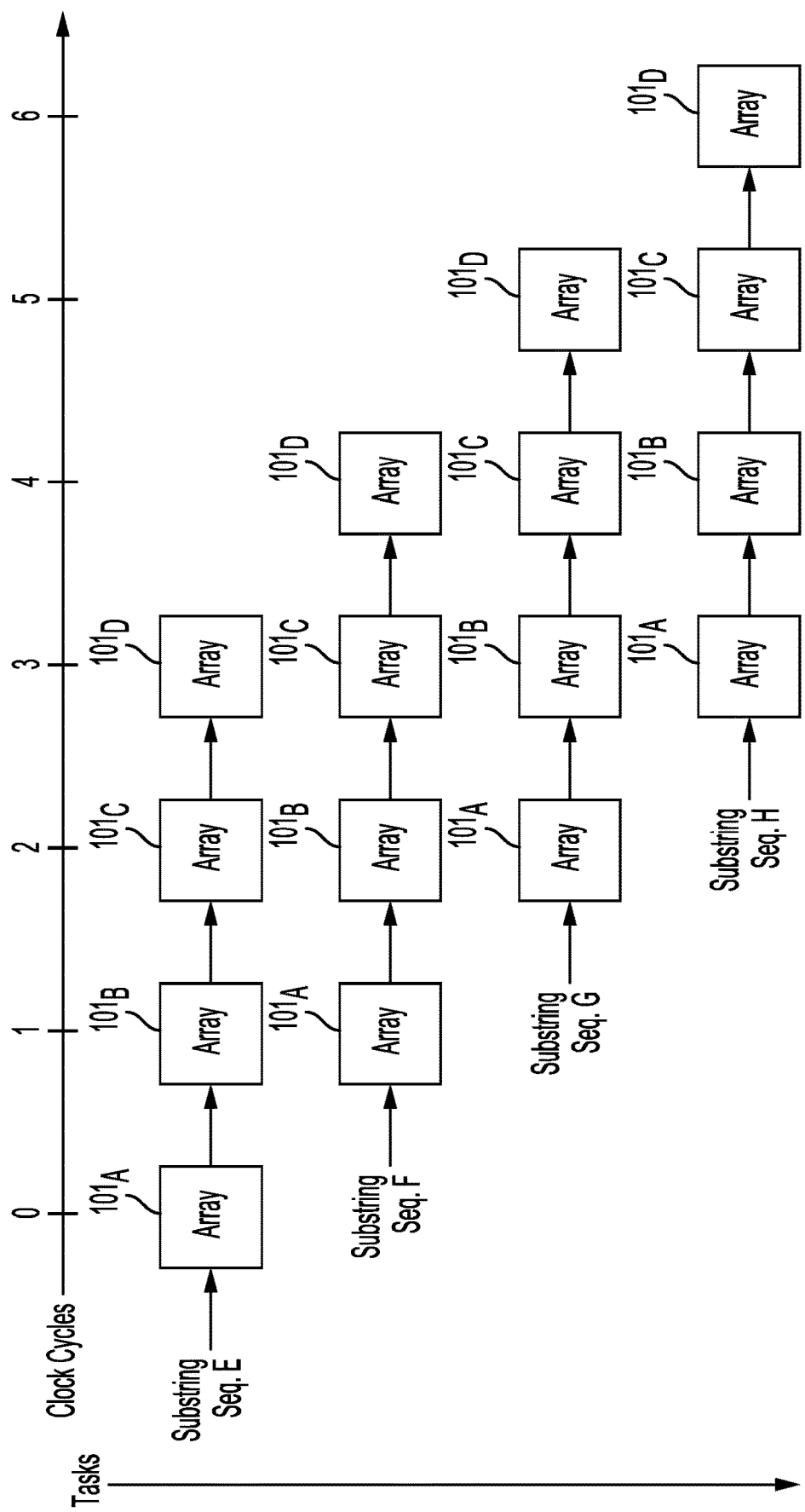
FIG. 7 illustrates an example of pipelining substring sequences according to one or more embodiments.

FIG. 7 illustrates an example of pipelining substring sequences according to one or more embodiments. As shown in FIG. 7, a substring sequence may be passed from one array to another array to compare the substring sequence to large number of reference sequences stored in the arrays. In addition, the different substring sequences may by cycled through the arrays to increase or maximize the number of arrays 101 being used during a given clock cycle to further improve processing efficiency. In some implementations, the substring sequence may be passed via control circuitry 104, or may be passed more directly from other circuitry such as program line and search line driver circuitry via interconnect 107.

In the example of FIG. 7, substring sequence E is fed from array $101_A$ to array $101_B$, to array $101_C$, and to array $101_D$ in successive clock cycles of device 100. After clock cycle 0, array $101_A$ becomes available to compare the next substring sequence to the reference sequences stored in array $101_A$. Substring sequence F is then loaded into array $101_A$ as substring sequence E is loaded into array $101_B$ during clock cycle 1.

In clock cycle 2, substring sequence G is loaded into array $101_A$, as substring sequence E is loaded into array $101_C$, and as substring sequence F is loaded into array $101_B$. At clock cycle 3, all four arrays 101 are in concurrent use comparing different substring sequences E, F, G, and H to the reference sequences stored in arrays $101_D$, $101_C$, $101_B$, and $101_A$, respectively. Within seven clock cycles, four different substring sequences are compared to reference sequences stored in all four arrays 101. As shown in the example of FIG. 7, the parallel or concurrent use of separate arrays 101 can improve the efficiency of sequencing by allowing for many concurrent comparisons in not only one array, but across multiple arrays 101 using a staggered or cycled approach.

Example Processes

Figure 8:
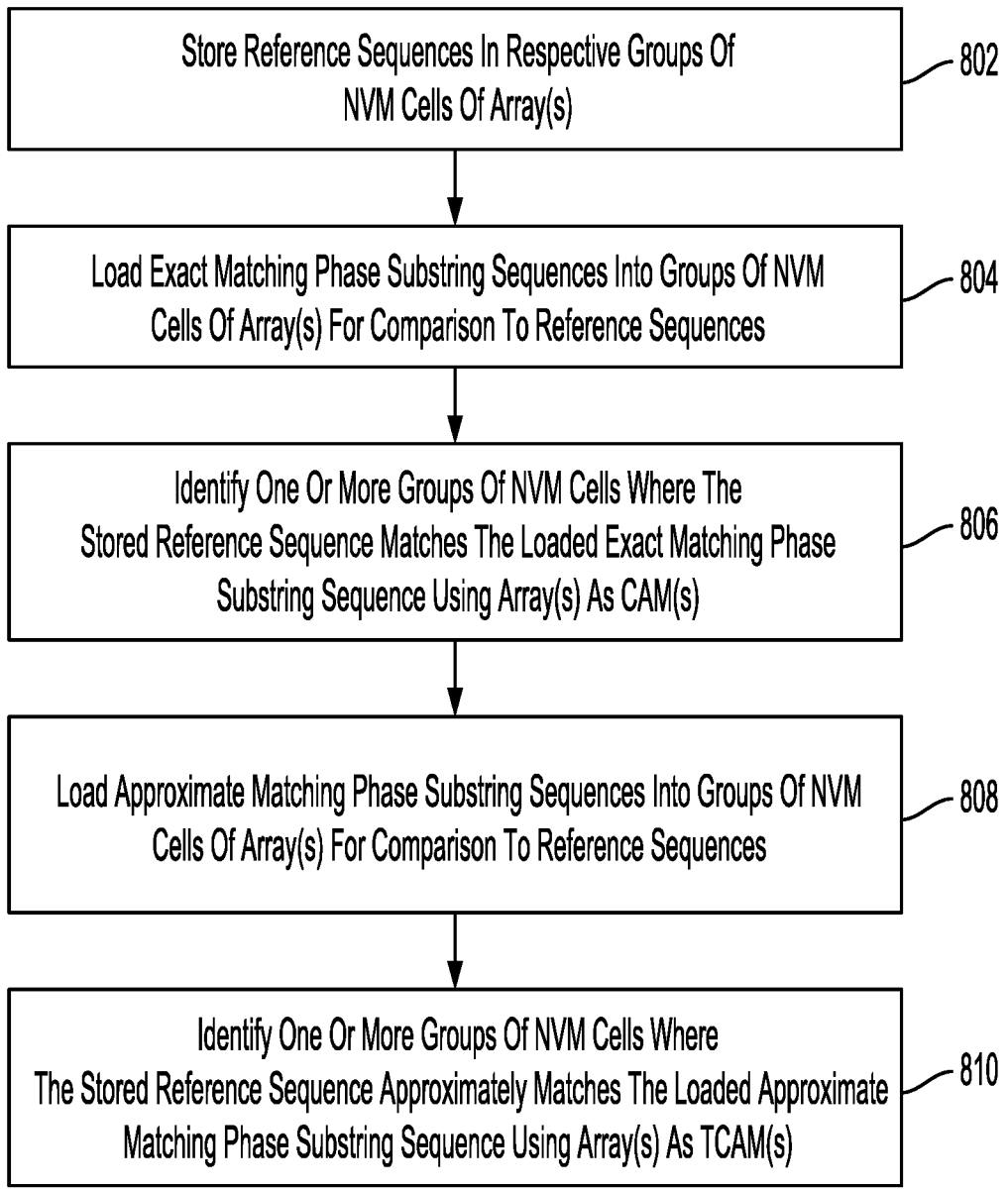
FIG. 8 is a flowchart for a genome sequencing process according to one or more embodiments.

FIG. 8 is a flowchart for a genome sequencing process including an exact matching phase and an approximate matching phase according to one or more embodiments. The process of FIG. 8 can be performed by, for example, control circuitry 104 of device 100.

In block 802, the circuitry stores reference sequences in respective groups of NVM cells of one or more arrays. The groups of NVM cells can include cells along a match line in an array. The reference sequences may be stored as a series of reference values that may be represented by resistance values set for resistors in the cell, such as for resistors M1 and M2 in FIG. 3.

In block 804, the circuitry loads exact matching phase substring sequences into groups of NVM cells of the one or more arrays. The loading of the exact matching phase substring sequences can represent an exact matching phase where the loaded substring sequences and the stored reference sequences do not include any wildcard values. In some implementations, an exact matching phase can be relatively quicker than an approximate matching phase, which may require more comparisons to be made and may require additional processing, such as with the population and evaluation of a scoring matrix, such as scoring matrix 20.

In block 806, one or more groups of NVM cells are identified where the stored reference sequence matches the loaded exact matching phase substring sequence. In some implementations, an exact matching phase substring sequence may be loaded into multiple arrays for a concurrent comparison to an entire reference genome or a relatively large portion of a reference genome represented by reference sequences stored in each group of cells in multiple arrays. In such implementations, one or more locations may be identified in the reference genome that match a loaded exact matching phase substring sequence. Indications of the identified groups of cells may be stored in a memory of the device, such as in memory 106 in FIG. 1 as part of index 10, for the circuitry to identify the one or more groups of NVM cells. In other implementations, indications of the identified groups of cells may be directly provided to the circuitry. In cases where there are multiple matches, the first matching location in the reference genome or first matching group of cells may be recorded, or alternatively, all matching locations or matching groups may be recorded, or none of the matching locations or matching groups may be recorded since the matches are not unique.

As discussed above, multiple substring sequences may be taken from a sample read to provide a probabilistic location within a reference genome based on the matching locations or matching groups of cells identified for the substring sequences of the sample read. For example, in some implementations, an average of the matching locations for a certain number of substring sequences taken from a sample read, such as ten substring sequences, may provide a probabilistic location for the sample read within the reference genome.

Based on the probabilistic locations, an approximate matching phase may be performed for a smaller partition of the reference genome to determine an optimal alignment of the sample read within the reference genome partition. In block 808, approximate matching phase substring sequences are loaded into groups of NVM cells of one or more arrays for approximate matching using a TCAM operation. At least one of the loaded approximate matching phase sequence and the stored reference sequence for each group of cells in the approximate matching phase include at least one wildcard value. Such approximate matching can accommodate read errors or mutations in the sample read. In addition, the use of approximate matching algorithms such as a Smith-Waterman algorithm or Automata-based algorithm can be used by a host, such as host 103 in FIG. 1, or by circuitry 104 to find an optimal or best fit alignment of a sample read within a sample genome by accounting for insertions, deletions, and mutations in the sample read.

In some implementations, the identified groups of cells from the exact matching phase may serve as a range of groups of cells that are used as a subset of the full number of groups of cells in the arrays, which may only include one or two arrays, for example, as opposed to a larger set of arrays used in the exact matching phase. In other implementations, a large set of substring sequences or sample reads may be narrowed down to a smaller set of non-matching substring sequences or sample reads after finding exact matches for a portion of the substring sequences or sample reads in the initial set. The remaining substring sequences or sample reads may then be located in a genome by using approximate matching during the approximate matching phase.

In block 810, one or more groups of NVM cells are identified where the stored reference sequence approximately matches the approximate matching phase substring sequence loaded in block 808. In some implementations, such as where a Smith-Waterman approximate matching algorithm is performed, a scoring matrix may be analyzed, such as by performing a traceback of scores stored in the scoring matrix to identify an optimal or best fit alignment of the approximate matching phase substring sequences in the reference genome or sample genome.

Those of ordinary skill in the art will appreciate with reference to the present disclosure that other implementations may include a different order of exact matching and approximate matching phases than discussed above for FIG. 8. For example, other implementations may perform an approximate matching phase before an exact matching phase, or may intermix exact matching and approximate matching phases. In one such example, a particular substring sequence may undergo exact matching and then approximate matching that is followed by exact matching and approximate matching phases for a different substring sequence. In addition, and as discussed above with reference to the concurrent processing examples of FIGS. 5 to 7, different arrays 101 in device 100 may be performing exact matching as a CAM, while other arrays 101 in device 100 perform approximate matching as a TCAM.

Figure 9:
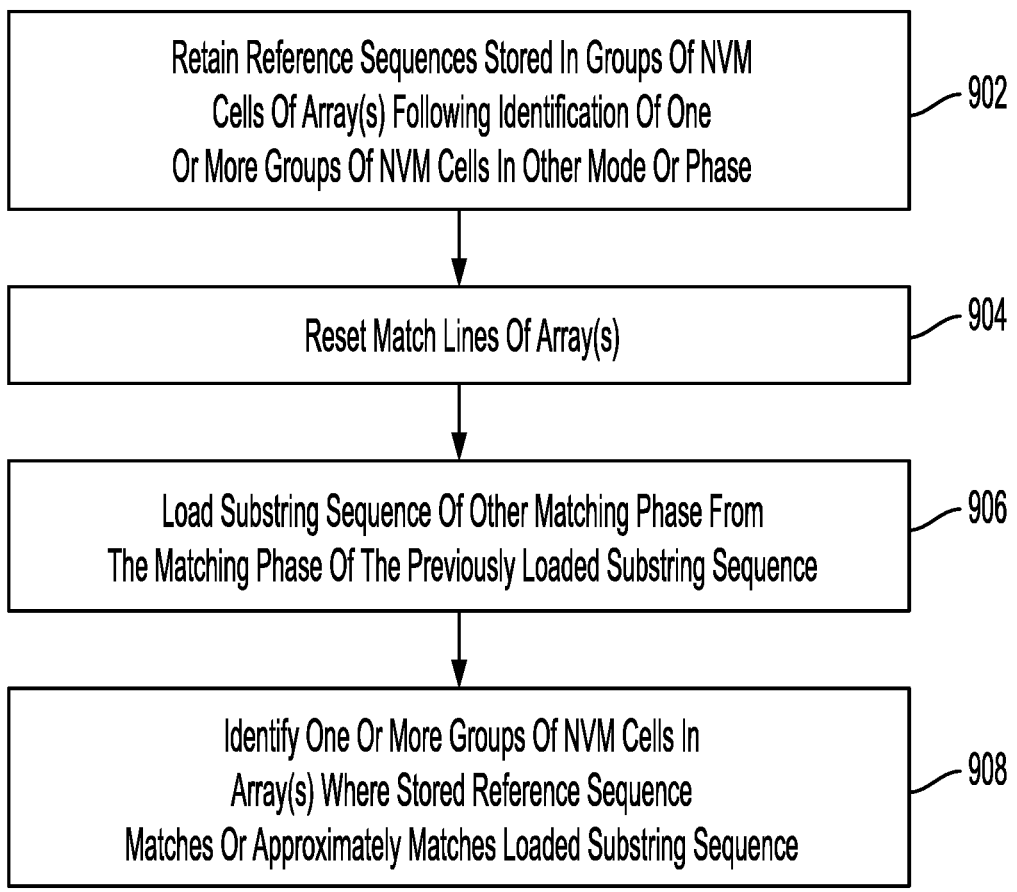
FIG. 9 is a flowchart for an operating mode switching process for at least one array of NVM cells according to one or more embodiments.

FIG. 9 is a flowchart for an operating mode switching process for at least one array of NVM cells according to one or more embodiments. The process of FIG. 9 can be performed by, for example, control circuitry 104 of device 100. In some implementations, the process of FIG. 9 may follow operation of the at least one array in a CAM mode for an exact matching phase. In other implementations, the process of FIG. 9 may follow operation of the at least one array in a TCAM mode for an approximate matching phase.

In block 902, reference sequences stored in groups of NVM cells of one or more arrays are retained following the identification of one or more groups of NVM cells in an earlier mode (e.g., a CAM or TCAM mode) or phase of operation (e.g., an exact matching or approximate matching phase). In this regard, the circuitry does not reset or clear the reference values stored in the groups of NVM cells, and thereby retains the reference sequences for use in the other mode or phase of operation. This can improve operating efficiency in some implementations when switching between exact matching and approximate matching phases, as compared to conventional genome sequencing that may require separate hardware and/or a separate storing or reprogramming of reference sequences for each matching phase.

In block 904, the circuitry resets match lines of the one or more arrays. In some implementations, this can include recharging match lines so that all the match lines or the previously non-matching match lines are raised to a charged state following the previous operation in the other mode or different phase. For example, match lines may be recharged that correspond to groups of cells where there was a mismatch in the previous operation between the reference sequence and the loaded substring sequence. In other implementations, resetting the match lines can include discharging match lines so that all the match lines or the previously matching match lines are lowered to ground.

In block 906, the circuitry loads a substring sequence of the other matching phase than the previously loaded substring sequence in the previous operation or phase. For example, if the previous operation was in the CAM mode for an exact matching phase, the previously loaded substring sequence may have included one or more wildcard values. The new substring sequence loaded in block 906 may then include wildcard values for operation in the TCAM mode for the approximate matching phase. On the other hand, if the previous operation was in the TCAM mode for an approximate matching phase, the previously loaded substring sequence may have included one or more wildcard values. The new substring sequence loaded in block 906 is then encoded so as not to include wildcard values for operation in the CAM mode for the exact matching phase.

In block 908, the circuitry identifies one or more groups of NVM cells in the at least one array where the stored reference sequence matches or approximately matches the loaded new substring sequence. The identification of the one or more groups of NVM cells may result from receiving one or more indications from encoding circuitry (e.g., encoder $116_A$ in FIG. 2) as to which match lines have a changed or maintained charge state. The control circuitry, for example, may receive the indications for identifying the matching groups of NVM cells directly from the encoding circuitry or from an intermediate memory, such as memory 106 in FIG. 1. Indications of the identified groups of cells may be stored in an index in some implementations, such as in index 10 in the example of FIG. 1.

As noted above, the retention of the stored reference sequences from one mode of operation to the other mode of operation (e.g., from CAM operation to TCAM operation or vice-versa) can allow for a relatively quick conversion from a first type of matching phase to a second type of matching phase using the same array or arrays. This ordinarily improves the operating or processing efficiency of the genome sequencing device, and can facilitate the reuse of the same array or arrays for both exact matching and approximate matching phases of the sequencing.

Figure 10:
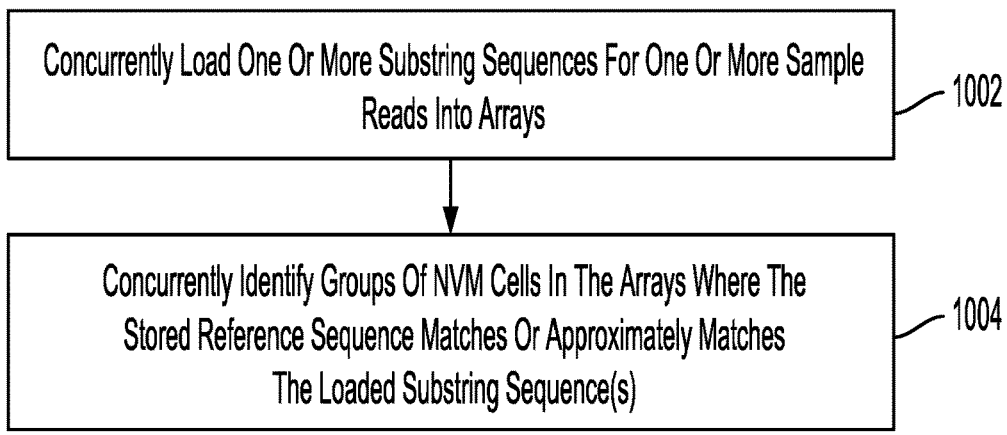
FIG. 10 is a flowchart for a concurrent matching process according to one or more embodiments.

FIG. 10 is a flowchart for a concurrent matching process according to one or more embodiments. The process of FIG. 10 can be performed by, for example, control circuitry 104 of device 100. As discussed above with reference to FIGS. 5 to 7, the concurrent use of multiple arrays of NVM cells can allow for a simultaneous or approximately simultaneous comparison of multiple substring sequences loaded into respective arrays to the reference sequences stored in the arrays. The use of an NVM CAM/TCAM cell structure can provide numerous comparisons corresponding to the number of the groups of NVM cells or match lines in a single operation or clock cycle of the device.

In block 1002, the circuitry concurrently loads one or more substring sequences for one or more sample reads into arrays including groups of NVM cells. In some implementations, the circuitry may load substring sequences that represent different portions of the same sample read. In such examples, the substring sequences may provide a probabilistic location for the sample read within a reference genome that is represented in whole or in part by the reference sequences stored in the arrays. In other examples, the loaded substring sequences may represent portions from different sample reads. In such examples, one or more arrays may be loaded with substring sequences from a first sample read, while one or more other arrays may be loaded with substring sequences from a second sample read. In yet other examples, a single substring sequence may be concurrently loaded into multiple arrays to perform a search for the loaded substring sequence across a large portion or an entirety of the genome represented by the reference sequences stored in the arrays.

In block 1004, the circuitry concurrently identifies groups of NVM cells in the arrays where the stored reference sequence matches or approximately matches the loaded substring sequence or sequences. In some implementations, the arrays and/or the one or more substring sequences may be programmed or encoded for exact matching. In other implementations, the arrays and/or the one or more substring sequences may be programmed or encoded for approximate matching to include wildcard values. The circuitry may identify groups of NVM cells where the stored reference sequence matches or approximately matches the loaded substring sequence based on indications received from encoders of the arrays (e.g., encoder $116_A$ in FIG. 2) or based on indications received from an intermediate memory (e.g., memory 106 in FIG. 2)

Figure 11:
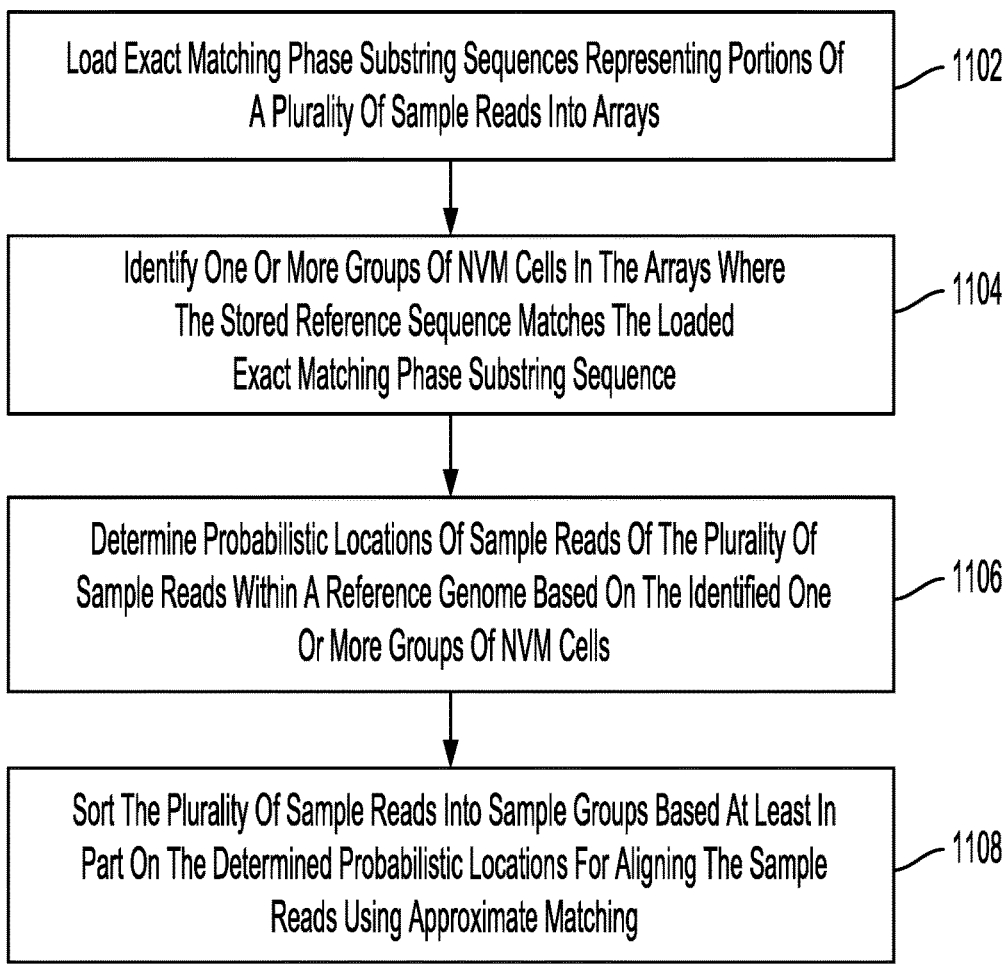
FIG. 11 is a flowchart for a sample read sorting process according to one or more embodiments.

FIG. 11 is a flowchart for a sample read sorting process according to one or more embodiments. The process of FIG. 11 can be performed by, for example, control circuitry 104 of device 100 and/or by host 103 in communication with device 100 to identify probabilistic locations of sample reads within a reference genome. The probabilistic locations may then be used to sort the sample reads into sample groups that can allow for additional comparisons of the sample reads to a smaller partition of the reference genome using approximate matching, as in the case of reference-aligned sequencing, or for additional comparisons of the sample reads in the sample group to each other using approximate matching, as in the case of de novo sequencing.

In block 1102, the circuitry loads exact matching phase substring sequences representing portions of a plurality of sample reads into arrays. A particular substring sequence may be loaded into multiple arrays at one time or clock cycle to identify potential matching locations within a reference genome represented by reference sequences stored across the multiple arrays. A different exact matching phase substring sequence from the same or a different sample read may then be loaded at a subsequent time or clock cycle. In other implementations, different exact matching phase substring sequences from the same sample read or from different sample reads may be loaded into different arrays at one time or clock cycle, and a next set of exact matching phase substring sequences from the same sample read or from different sample reads may then be loaded at a subsequent time or clock cycle.

In block 1104, one or more groups of NVM cells in the arrays are identified where the stored reference sequence matches the loaded exact matching phase substring sequence. The identification of the one or more groups of NVM cells may be performed by circuitry, such as sense and latch circuitry for the arrays (e.g., sense and latch circuitry 114A in FIG. 2), that reads or senses the states of match lines for the groups of NVM cells.

In block 1106, control circuitry of the device (e.g., control circuitry 104 in FIG. 1) or a host in communication with the device (e.g., host 103 in FIG. 1) determines probabilistic locations of the sample reads within a reference genome based on the identified one or more groups of NVM cells. The control circuitry or host may use indications of identified groups of cells stored in an index or other data structure to determine the probabilistic or approximate locations of the sample reads. For example, with reference to FIG. 1, memory 106 may store index 10 that may indicate an average of multiple locations identified for different substring sequences of the same sample read. The locations for the sample reads determined in block 1106 can be probabilistic in the sense that multiple possible locations can be identified for different substring sequences from a sample read, and a consensus or statistic derived from the matching locations can be used to probabilistically locate the sample read within the reference genome.

In one example, a mean of all the identified locations of the matching groups of NVM cells for a substring sequence for a sample read is used to identify a most likely location of the sample read within the reference genome. In another example, only one location for each substring sequence with a matching group of cells is used in the mean. In yet another example, a probabilistic location of the sample read may be determined by identifying the farthest apart locations within the reference genome that correspond to matching groups of NVM cells for the substring sequences from the sample read. In other examples, one or more outlier locations with respect to a group of matching locations may be discarded in determining the probabilistic location of the sample read within the reference genome.

In block 1108, the circuitry or the host sorts the plurality of sample reads into sample groups based at least in part on the determined probabilistic locations for the sample reads for aligning the sample reads using approximate matching. In this regard, the exact matching performed by device 100 in the process of FIG. 11 may be followed by an approximate matching phase performed by device 100 to find a best fit or optimal alignment of sample reads to a smaller partition of the reference genome that is associated with the sample group. In other implementations, the following approximate matching phase performed by device 100 may use approximate matching to find a best fit or optimal alignment of the sample reads with respect to the other sample reads in the sample group. In both cases, the computational complexity and processor hours for performing the approximate matching phase is significantly reduced by sorting the sample reads into the sample groups due to the smaller partition of the reference genome or the smaller number of sample reads being compared to each other in each sample group.

Those of ordinary skill in the art will appreciate with reference to the present disclosure that the order of the blocks of FIG. 11 may differ in other implementations. For example, blocks 1102 to 1106 may be performed as an iterative set for each sample read before performing the sorting of sample reads in block 1108. In other examples, the probabilistic location of each sample read may be sorted on the fly for predetermined or dynamically changing partitions of the reference genome for successive iterations of the process for one sample read at a time. In yet other implementations, the circuitry may determine the groups of sample reads for sorting after determining probabilistic locations for all the sample reads so that the groups of sample reads include approximately the same number of sample reads or cover approximately the same range of bases in the reference genome.

As discussed above, the foregoing examples of devices including arrays of NVM cells that can operate as either a CAM or a TCAM depending on the programming or encoding, can ordinarily improve the processing efficiency and reduce the physical size of genome sequencing devices. In this regard, the reuse of the same arrays for both exact matching when operating as a CAM and approximate matching when operating as a TCAM can reduce the amount of storage needed for the different types of matching and may allow for the reuse of stored reference sequences for different phases or for different substring sequences representing one or more sample reads. In addition, the non-volatile nature of the arrays disclosed herein can reduce the energy requirements for performing sequencing as compared to SRAM arrays, while still obtaining the benefits of the fast matching offered by CAMs.

Other Embodiments

Those of ordinary skill in the art will appreciate that the various illustrative logical blocks, modules, and processes described in connection with the examples disclosed herein may be implemented as electronic hardware, software, or combinations of both. Furthermore, the foregoing processes can be embodied on a computer readable medium which causes a processor, controller, or other circuitry to perform or execute certain functions.

To clearly illustrate this interchangeability of hardware and software, various illustrative components, blocks, and modules have been described above generally in terms of their functionality. Whether such functionality is implemented as hardware or software depends upon the particular application and design constraints imposed on the overall system. Those of ordinary skill in the art may implement the described functionality in varying ways for each particular application, but such implementation decisions should not be interpreted as causing a departure from the scope of the present disclosure.

The various illustrative logical blocks, units, modules, and circuitry described in connection with the examples disclosed herein may be implemented or performed with a general purpose processor, a GPU, a DSP, an ASIC, an FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. Processor or controller circuitry may also be implemented as a combination of computing devices, e.g., a combination of a DSP and a microprocessor, a plurality of microprocessors, an SoC, one or more microprocessors in conjunction with a DSP core, or any other such configuration.

The activities of a method or process described in connection with the examples disclosed herein may be embodied directly in hardware, in a software module executed by processor or other circuitry, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable media, an optical media, or any other form of storage medium known in the art. An exemplary storage medium is coupled to processor or controller circuitry such that the processor or controller circuitry can read information from, and write information to, the storage medium. In the alternative, the storage medium may be integral to processor or controller circuitry. The processor or controller circuitry and the storage medium may reside in an ASIC or an SoC.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the spirit or scope of the present disclosure. The described embodiments are to be considered in all respects only as illustrative and not restrictive. In addition, the use of language in the form of "at least one of A and B" in the following claims should be understood to mean "only A, only B, or both A and B."

What is claimed is:

1. A device, comprising:
a plurality of arrays of Non-Volatile Memory (NVM) cells; and
circuitry configured to:
store reference sequences in respective groups of NVM cells of the plurality of arrays, each reference sequence representing a portion of a genome;
load one or more exact matching phase substring sequences into groups of NVM cells of the plurality of arrays for comparison to reference sequences stored in the groups of NVM cells, the one or more exact matching phase substring sequences representing portions of at least one sample read;
identify, in an exact matching phase, one or more groups of NVM cells in the plurality of arrays where the stored reference sequence matches the loaded exact matching phase substring sequence using the plurality of arrays as Content Addressable Memories (CAMs), wherein none of the compared reference sequences and the one or more exact matching phase substring sequences include wildcard values when using the plurality of arrays as CAMs in the exact matching phase;

load one or more approximate matching phase substring sequences into groups of NVM cells of the plurality of arrays for comparison to reference sequences stored in the groups of NVM cells, the one or more approximate matching phase substring sequences representing portions of the at least one sample read;

identify, in an approximate matching phase, one or more groups of NVM cells in the plurality of arrays where the stored reference sequence approximately matches the loaded approximate matching phase substring sequence using the plurality of arrays as Ternary CAMs (TCAMs), wherein at least one of the compared reference sequence and the approximate matching phase substring sequence for each group of NVM cells includes at least one wildcard value when using the plurality of arrays as TCAMs in the approximate matching phase; and based on an indication of one or more identified groups of NVM cells from a first array of the plurality of arrays where one or more stored reference sequences match or approximately match a first substring sequence, perform at least one of:
store one or more additional reference sequences in a second array of the plurality of arrays; and
load at least one additional substring sequence into the second array.

2. The device of claim 1, wherein the circuitry is further configured to vary an encoding scheme for the reference sequences, the one or more exact matching phase substring sequences, and the one or more approximate matching phase substring sequences to switch between operation of the plurality of arrays as CAMs and as TCAMs.

3. The device of claim 1, wherein for the approximate matching phase, the circuitry is further configured to:
retain reference sequences stored in groups of NVM cells of an array of the plurality of arrays following operation of the array as a CAM in the exact matching phase;
reset match lines of the array;
load at least one approximate matching phase substring sequence into the groups of NVM cells of the array; and
identify one or more groups of NVM cells in the array where the stored reference sequence approximately matches the loaded at least one approximate matching phase substring sequence for operation of the array as a TCAM in the approximate matching phase.

4. The device of claim 1, wherein for the exact matching phase, the circuitry is further configured to:
retain reference sequences stored in groups of NVM cells of an array of the plurality of arrays following operation of the array as a TCAM in the approximate matching phase;
reset match lines of the array;
load at least one exact matching phase substring sequence into the groups of NVM cells of the array; and
identify one or more groups of NVM cells in the array where the stored reference sequence matches the loaded at least one exact matching phase substring sequence for operation of the array as a CAM in the exact matching phase.

5. The device of claim 1, wherein for at least one of the exact matching phase and the approximate matching phase, the circuitry is further configured to:
concurrently load one or more substring sequences into arrays of the plurality of arrays; and
concurrently identify groups of NVM cells in the arrays where the stored reference sequence matches or approximately matches the concurrently loaded one or more substring sequences.

6. The device of claim 5, wherein the concurrently loaded one or more substring sequences includes substring sequences that represent different portions of the same sample read.

7. The device of claim 1, wherein the number of NVM cells used to represent a base of an approximate matching phase substring sequence in at least one group of NVM cells in the plurality of arrays differs from the number of NVM cells used to represent a base of an exact matching phase substring sequence in the at least one group of NVM cells.

8. The device of claim 1, further comprising at least one memory configured to store an index indicating identified groups of NVM cells where the stored reference sequence approximately matches or matches a loaded substring sequence.

9. The device of claim 1, further comprising at least one memory configured to store a Smith-Waterman scoring matrix used during an approximate matching phase.

10. The device of claim 1, wherein for the exact matching phase, the circuitry is further configured to:
load, into arrays of the plurality of arrays, exact matching phase substring sequences of the one or more exact matching phase substring sequences, wherein the exact matching phase substring sequences represent portions from a plurality of sample reads;
identify one or more groups of NVM cells in the arrays where the stored reference sequence matches the loaded exact matching phase substring sequences, wherein each stored reference sequence represents a portion of a reference genome;
determine probabilistic locations of the plurality of sample reads within the reference genome based on the identified one or more groups of NVM cells; and
sort the plurality of sample reads into a plurality of sample groups based at least in part on the determined probabilistic locations of the respective sample reads for aligning the sample reads using approximate matching.

11. A method of genome sequencing, the method comprising:
storing reference sequences in respective groups of Non-Volatile Memory (NVM) cells of at least one array of NVM cells, each reference sequence representing a portion of a genome;
loading one or more exact matching phase substring sequences into groups of NVM cells of the at least one array for operation of the at least one array as a Content Addressable Memory (CAM), the one or more exact matching phase substring sequences representing one or more portions of at least one sample read;
identifying, in an exact matching phase, one or more groups of NVM cells in the at least one array where the stored reference sequence matches the loaded exact matching phase substring sequence, wherein none of the stored reference sequences and the loaded one or more exact matching phase substring sequences include wildcard values when the at least one array operates as a CAM in the exact matching phase;
loading one or more approximate matching phase substring sequences into groups of NVM cells of the at least one array for operation of the at least one array as a Ternary CAM (TCAM), the one or more approximate matching phase substring sequences representing one or more portions of the at least one sample read;

identifying, in an approximate matching phase, one or more groups of NVM cells in the at least one array where the stored reference sequence approximately matches the loaded approximate matching phase sequence, wherein at least one of the stored reference sequence and the loaded approximate matching phase substring sequence for each group of NVM cells includes at least one wildcard value when the at least one array operates as a TCAM in the approximate matching phase; and based on an indication of one or more identified groups of NVM cells from a first array of the at least one array where one or more stored reference sequences match or approximately match a first substring sequence, performing at least one of:
storing one or more additional reference sequences in a second array of the at least one array; and
loading at least one additional substring sequence into the second array.

12. The method of claim 11, further comprising varying an encoding scheme for the reference sequences, the one or more exact matching phase substring sequences, and the one or more approximate matching phase substring sequences to switch between operation of the at least one array as a CAM and as a TCAM.

13. The method of claim 11, further comprising for the approximate matching phase:
retaining reference sequences stored in groups of NVM cells of an array of the at least one array following operation of the array as a CAM in the exact matching phase;
resetting match lines of the array;
loading at least one approximate matching phase sequence into the groups of NVM cells of the array; and
identifying one or more groups of NVM cells in the array where the stored reference sequence approximately matches the loaded at least one approximate matching phase sequence for operation of the array as a TCAM in the approximate matching phase.

14. The method of claim 11, further comprising for the exact matching phase:
retaining reference sequences stored in groups of NVM cells of an array of the at least one array following operation of the array as a TCAM in the approximate matching phase;
resetting match lines of the array;
loading at least one exact matching phase substring sequence into the groups of NVM cells of the array; and
identifying one or more groups of NVM cells in the array where the stored reference sequence matches the loaded at least one exact matching phase substring sequence for operation of the array as a CAM in the exact matching phase.

15. The method of claim 11, further comprising for at least one of the exact matching phase and the approximate matching phase:
concurrently loading one or more substring sequences for one or more sample reads into arrays of the at least one array; and
concurrently identifying groups of NVM cells in the arrays where the stored reference sequence matches or approximately matches the concurrently loaded one or more substring sequences.

16. The method of claim 15, wherein the concurrently loaded one or more substring sequences include substring sequences representing different portions of the same sample read.

17. The method of claim 11, wherein the number of NVM cells used to represent a base of an approximate matching phase substring sequence in at least one group of NVM cells in the at least one array differs from the number of NVM cells used to represent a base of an exact matching phase substring sequence in the at least one group of NVM cells.

18. The method of claim 11, further comprising storing in at least one memory indications of identified groups of NVM cells where the stored reference sequence approximately matches or matches a loaded substring sequence.

19. The method of claim 11, further comprising for the exact matching phase:
loading, into the at least one array, exact matching phase substring sequences of the one or more exact matching substring sequences, wherein the exact matching phase substring sequences represent portions from a plurality of sample reads;
identifying one or more groups of NVM cells in the at least one array where the stored reference sequence matches the loaded exact matching phase substring sequences, wherein each stored reference sequence represents a portion of a reference genome;
determining probabilistic locations of the plurality of sample reads within the reference genome based on the identified one or more groups of NVM cells; and
sorting the plurality of sample reads into a plurality of sample groups based at least in part on the determined probabilistic locations of the respective sample reads for aligning the sample reads using approximate matching.

20. A device for genome sequencing, the device comprising:
at least one array of Non-Volatile Memory (NVM) cells configured to store reference sequences in respective groups of the NVM cells, each reference sequence representing a portion of a genome; and
means for:
storing the reference sequences in the respective groups of NVM cells of the at least one array;
loading one or more exact matching phase substring sequences into groups of NVM cells of the at least one array for operation of the at least one array as a Content Addressable Memory (CAM), the one or more exact matching phase substring sequences representing one or more portions of at least one sample read;
identifying, in an exact matching phase, one or more groups of NVM cells in the at least one array where the stored reference sequence matches the loaded exact matching phase substring sequence, wherein none of the stored reference sequences and the loaded one or more exact matching phase substring sequences include wildcard values when the at least one array operates as a CAM in the exact matching phase;
loading one or more approximate matching phase substring sequences into groups of NVM cells of the at least one array for operation of the at least one array as a Ternary CAM (TCAM), the one or more approximate matching phase substring sequences representing one or more portions of the at least one sample read; and
identifying, in an approximate matching phase, one or more groups of NVM cells in the at least one array where the stored reference sequence approximately matches the loaded approximate matching phase sequence, wherein at least one of the stored reference sequence and the loaded approximate matching phase substring sequence for each group of NVM cells includes at least one wildcard value when the at least one array operates as a TCAM in the approximate matching phase; and wherein at least one group of NVM cells in the at least one array is used as part of a CAM in the exact matching phase and is used as part of a TCAM in the approximate matching phase, and wherein the number of NVM cells used to represent a base of an approximate matching phase substring sequence in the at least one group of NVM cells differs from the number of NVM cells used to represent a base of an exact matching phase substring sequence in the at least one group of NVM cells.

21. A device, comprising:

a plurality of arrays of Non-Volatile Memory (NVM) cells capable of operating in a Content Addressable Memory (CAM) mode and a Ternary CAM (TCAM) mode; and circuitry configured to:
- store reference sequences in respective groups of NVM cells of the plurality of arrays;
- load one or more exact matching phase substring sequences into groups of NVM cells of the plurality of arrays;
- set the plurality of arrays in the CAM mode and identify, in an exact matching phase, one or more groups of NVM cells where the stored reference sequence matches the loaded exact matching phase substring sequence;
- load one or more approximate matching phase substring sequences into groups of NVM cells of the plurality of arrays; and
- set the plurality of arrays in the TCAM mode and identify, in an approximate matching phase, one or more groups of NVM cells where the stored reference sequence approximately matches the loaded approximate matching phase substring sequence, wherein at least one of the compared reference sequence and the approximate matching phase substring sequence includes at least one wildcard value in the approximate matching phase; and
- wherein at least one group of NVM cells in the plurality of arrays is used as a CAM in the exact matching phase and is used as a TCAM in the approximate matching phase, and wherein the number of NVM cells used to represent a base of an approximate matching phase substring sequence in the at least one group of NVM cells differs from the number of NVM cells used to represent a base of an exact matching phase substring sequence in the at least one group of NVM cells.

22. The device of claim 21, wherein the circuitry is further configured to vary an encoding scheme for the reference sequences, the one or more exact matching substring sequences, and the one or more approximate matching substring sequences to switch between operation of the plurality of arrays in the CAM and TCAM modes.

23. The device of claim 21, wherein a pair of values is loaded or stored in an NVM cell to represent a wildcard value in the approximate matching phase.

24. The device of claim 21, wherein the circuitry is further configured to use an indication of one or more identified groups of NVM cells from a first array of the plurality of arrays where one or more stored reference sequences match or approximately match a first substring sequence for at least one of:
- determining one or more additional reference sequences to be stored in a second array of the plurality of arrays; and
- determining at least one additional substring sequence to be loaded into the second array.

25. The device of claim 21, wherein for at least one of the exact matching phase and the approximate matching phase, the circuitry is further configured to:
- concurrently load one or more substring sequences into arrays of the plurality of arrays; and
- concurrently identify groups of NVM cells in the arrays where the stored reference sequence matches or approximately matches the concurrently loaded one or more substring sequences.

26. The device of claim 25, wherein the concurrently loaded one or more substring sequences includes substring sequences that represent different portions of the same sample read.

* * * * *